United States Patent
Grandori et al.

(10) Patent No.: US 9,801,853 B2
(45) Date of Patent: Oct. 31, 2017

(54) METHODS FOR IDENTIFYING AND USING INHIBITORS OF CASEIN KINASE 1 EPSILON ISOFORM FOR INHIBITING THE GROWTH AND/OR PROLIFERATION OF MYC-DRIVEN TUMOR CELLS

(75) Inventors: Carla Grandori, Seattle, WA (US); Masafumi Toyoshima, Seattle, WA (US)

(73) Assignee: Fred Hutchinson Cancer Research Center, Seattle, WA (US)

( * ) Notice: Subject to any disclaimer, the term of this patent is extended or adjusted under 35 U.S.C. 154(b) by 0 days.

(21) Appl. No.: 13/639,258

(22) PCT Filed: Apr. 6, 2011

(86) PCT No.: PCT/US2011/031460
§ 371 (c)(1),
(2), (4) Date: Dec. 27, 2012

(87) PCT Pub. No.: WO2011/127202
PCT Pub. Date: Oct. 13, 2011

(65) Prior Publication Data
US 2013/0115309 A1     May 9, 2013

Related U.S. Application Data

(60) Provisional application No. 61/321,414, filed on Apr. 6, 2010.

(51) Int. Cl.
| | | |
|---|---|---|
| A61K 31/404 | (2006.01) | |
| A61K 31/506 | (2006.01) | |
| A61K 31/519 | (2006.01) | |
| A61K 33/24 | (2006.01) | |

(52) U.S. Cl.
CPC .......... *A61K 31/404* (2013.01); *A61K 31/506* (2013.01); *A61K 31/519* (2013.01); *A61K 33/24* (2013.01)

(58) Field of Classification Search
CPC .................................................. A61K 31/404
See application file for complete search history.

(56) References Cited

U.S. PATENT DOCUMENTS

| | | |
|---|---|---|
| 9,273,317 B2 | 3/2016 | Toyoshima et al. |
| 2005/0002998 A1 | 1/2005 | Chang et al. |
| 2007/0099209 A1 | 5/2007 | Clarke et al. |
| 2007/0105114 A1 | 5/2007 | Li et al. |
| 2010/0179154 A1* | 7/2010 | Almario Garcia et al. .. 514/248 |
| 2013/0065939 A1 | 3/2013 | Judge et al. |
| 2015/0148401 A1 | 5/2015 | Toyoshima et al. |
| 2016/0289686 A1 | 10/2016 | Kemp et al. |
| 2016/0367572 A1 | 12/2016 | Toyoshima et al. |

FOREIGN PATENT DOCUMENTS

| | | |
|---|---|---|
| FR | 2918061 | 1/2009 |
| WO | WO 2004/035076 | 4/2004 |
| WO | WO 2005/056043 | 6/2005 |
| WO | 2007-513940 A | 5/2007 |
| WO | WO 2009/016286 A2 | 2/2009 |
| WO | WO 2009/145815 * | 12/2009 |
| WO | WO 2010/111712 A2 | 9/2010 |
| WO | WO 2011/127202 | 10/2011 |
| WO | WO 2013/023084 | 2/2013 |
| WO | WO 2013/023084 A2 | 2/2013 |
| WO | WO 2015/077602 A1 | 5/2015 |

OTHER PUBLICATIONS

Cheong et al. IC261 induces cell cycle arrest and apoptosis of human cancer cells via CK1 delta/epsilon and Wnt/beta-catenin independent inhibition of mitotic spindle formation. Oncogene, 2001, 30, 2558-2569.*

Schleger et al. c-myc activation in primary and metastatic ductal adenocarcinoma of the pancreas: incidence, mechanisms and clinical significance. Mod. Pathol. 2002; 15(4): 462-469).*

Tashiro et al. c-myc over-expression in human primary ovarian tumours: its relevants to tumour progression. Int. J. Cancer: 50, 828-833, 1992.*

Brockschmidt. Anti-apoptotic and growth-stimulatory functions of CK1 delta and epsilon in ductal adenocarcinoma of the pancrase are inhibited by IC261 in vitro and in vivo. Pancreas. Gut, 2008; 57: 799-806.*

Behrend et al. IC261, a specific inhibitor of the protein kinases casein kinase 1-delta and -epsilon, triggers the mitotic checkpoint and induces p53-dependent postmitotic effects. Oncogene, 2000, 19, 5303-5313.*

Yang et al. Inhibition of casein kinase I-epsilon induces cancer-cell-selective, PERIOD2 dependent growth arrest. Genome Biology, 2008, 9: R92.*

Kikuchi et al. Treatment options in the management of ovarian cancer. (Expert Opinion on pharmacotherapy, 2005, 743-754).*

Iba et al. Expression of the c-myc gene as a predictor of chemotherapy response and a prognostic factor in patients with ovarian cancer. Cancer Science, May 2004, vol. 95, No. 5.*

Smal et al. Casein kinase 1 delta activates human recombinant deoxycytidine kinase by Ser-74 phosphorylation, but is not involved in the in vivo regulation of its activity. Archives of Biochemistry and Biophysics, 502 (2010): 44-52.*

Supplemental European Search Report, EP 11766677.6, dated Oct. 7, 2103.

Chung, et al., "MicroRNA-21 promotes the ovarian teratocarcinoma PA1 cell line by sustaining cancer stem/progenitor populations in vitro," Stem Cell Research and Therapy, 4(88):1-10 (2013).

Goga, et al., "Inhibition of CDK1 as a potential therapy for tumors over-expressing MYC," Nature Medicine, 13(7):820-827 (2007).

(Continued)

*Primary Examiner* — Theodore R. West
(74) *Attorney, Agent, or Firm* — Cooley LLP

(57) ABSTRACT

In one aspect, the invention provides a method for inhibiting the growth and/or proliferation of a myc-driven tumor cell comprising the step of contacting the tumor cells with a CSNK1ε inhibitor. In another aspect, the invention provides a method of treating a subject suffering from a tumor comprising myc-driven tumor cells, comprising administering to the subject an amount of a composition comprising a CSNK1ε inhibitor effective to inhibit the growth and/or proliferation of the tumor cells.

21 Claims, 25 Drawing Sheets

(56) References Cited

OTHER PUBLICATIONS

Grinshtein, et al., "Small Molecule Kinase Inhibitor Screen Identifies Polo-Like Kinase 1 as a Target for Neuroblastoma Tumor-Initiating Cells," Cancer Research, 71:1385-1395 (2011).
PJ, Chiao, et al., "Susceptibility to ras oncogene transformation is coregulated with signal transduction through growth factor receptors," Oncogene, 6(5):Abstract (1991).
Russo, et al., "c-myc Down-Regulation Induces Apoptosis in Human Cancer Cell Lines Exposed to RPR-115135 (C31H29NO4), a Non-Peptidomimetic Farnesyltransferase Inhibitor," Journal of Pharmacology and Experimental Therapeutics, 304(1):37-47 (2002).
Sarraf, et al., "The human ovariam teratocarcinoma call line PA-1 demonstrates a single translocation: analysis with fluorescence in situ hybridization, spectral karyotyping, and bacterial artificel chromosome microarray," Cancer Genetics and Cytogenetics, 161:63-69 (2005).
Tainsky, et al., "OA-1, A Human Cell Model for Multistage Carcinogensis: Oncogenes and Other Factors," Anticancer Research, 8:899-914 (1988).
Tashiro, et al., "c-myc Over-Expression in Human Primary Overian Tumours: Its Relevance to Tumour Progression," Int. J. Cancer, 50:828-833 (1992).
Walton, et al., "Selective Inhibition of Casein Kinase 1 epsilon Minimally Alters Circadian Clock Period," Journal of Pharmacology and Experimental Therapeutics, 330(2): 430-439 (2009).
International Search Report for International Application No. PCT/US2012/050186, dated Apr. 18, 2013.
Written Opinion for International Application No. PCT/US2012/050186, dated Apr. 18, 2012.
International Preliminary Report on Patentability for International Application No. PCT/US2012/050186, dated Feb. 11, 2014.
Arabi, et al., "c-Myc associates with ribosomal DNA and activates RNA polymerase I transcription," Nat Cell Biol 7(3):303-310 (2005).
Barna, et al., "Suppression of Myc oncogenic activity by ribosomal protein haploinsufficiency," Nature 456(7224):971-975 (2008).
Bartz, et al., "Small interfering RNA screens reveal enhanced cisplatin cytotoxicity in tumor cells having both BRCA network and TP53 disruptions," Mol Cell Biol 26(24):9377-9386 (2006).
Benanti, et al., "Epigenetic down-regulation of ARF expression is a selection step in immortalization of human fibroblasts by c-Myc," Mol Cancer Res 5 (11), 1181-1189 (2007).
Benanti, et al., "Normal human fibroblasts are resistant to RAS-induced senescence," Mol Cell Biol 24 (7), 2842-2852 (2004).
Berns, et al., c-myc amplification is a better prognostic factor than HER2/neu amplification in primary breast cancer. Cancer Res 52 (5), 1107-1113 (1992).
Blancato, et al., "Correlation of amplification and overexpression of the c-myc oncogene in high-grade breast cancer: FISH, in situ hybridisation and immunohistochemical analyse,". Br J Cancer 90 (8), 1612-1619 (2004).
Boon, et al., "N-myc enhances the expression of a large set of genes functioning in ribosome biogenesis and protein synthesis," EMBO J 20(6):1383-1393 (2001).
Campaner, et al., "Cdk2 suppresses cellular senescence induced by the c-myc oncogene," Nat Cell Biol 12(1):54-59; sup pp. 51-14 (2010).
Chen, et al., "Overexpression of c-Myc were obsereved in 66% of Epithelial Ovarian Cancers (EOCs)," Int J Gynecol Cancer, 15(5):878-883, 2005.
Chung, et al., "Median absolute deviation to improve hit selection for genome-scale RNAi screens," J Biomol Screen 13(2):149-158 (2008).
Cole, et al., "RNAi screen of the protein kinome identifies checkpoint kinase 1 (CHK1) as a therapeutic target in neuroblastoma," Proceedings of the National Academy of Sciences, 108(8):3336-3341 (2011).

Cowling, et al., "Turning the tables: Myc activates Wnt in breast cancer," Cell Cycle 6(21):2625-2627 (2007).
Dharcy, et al., "c-MYC amplification was observed in 29% (28/97) of EOCs by FISH analysis," Gynecol Oncol, 114(3):472-479 (2009).
Dominguez-Sola, et al., "Non-transcriptional control of DNA replication by c-Myc," Nature 448(7152):445-451 (2007).
Firestein, et al., "CDK8 is a colorectal cancer oncogene that regulates beta-catenin activity," Nature 455(7212):547-551 (2008).
Grandori, et al., "c-Myc binds to human ribosomal DNA and stimulates transcription of rRNA genes by RNA polymerase I," Nat Cell Biol 7(3):311-318 (2005).
Grandori, et al., "Myc-Max heterodimers activate a DEAD box gene and interact with multiple E box-related sites in vivo," EMBO Journal 15(16):4344-4357 (1996).
Grandori, et al., "Werner syndrome protein limits MYC-induced cellular senescence," Genes Dev 17(13):1569-1574 (2003).
Greer, et al., "Casein kinase 1 delta functions at the centrosome to mediate Wnt-3a-dependent neurite outgrowth," J Cell Biol, 192(6):993-1004 (2011).
Hanks, et al., "Protein kinases 6. The eukaryotic protein kinase superfamily: kinase (catalytic) domain structure and classification," Faseb J 9(8):576-596 (1995).
Hopkins, et al., "The druggable genome," Nat Rev Drug Discov 1(9):727-730 (2002).
Jenkins, et al., "Detection of c-myc oncogene amplification and chromosomal anomalies in metastatic prostatic carcinoma by fluorescence in situ hybridization," Cancer Res 57 (3), 524-531 (1997).
Kim, et al., "CK1epsilon is required for breast cancers dependent on beta-catenin activity," PLoS One 5(2):8979, Feb. 2010.
Kozma, et al., "Investigation of c-myc oncogene amplification in colorectal cancer," Cancer Lett 81 (2), 165-169 (1994).
Luts, et al., "Conditional expression of N-myc in human neuroblastoma cells increases expression of alpha-prothymosin and ornithine decarboxylase and accelerates progression into S-phase early after mitogenic stimulation of quiescent cells,:" Oncogene 13(4):803-812 (1996).
Major, et al., "New regulators of Wnt/beta-catenin signaling revealed by integrative molecular screening," Sci Signal 1(45):ra12 (2008).
Malynn, et al., "N-myc can functionally replace c-myc in murine development, cellular growth, and differentiation," Genes Dev 14(11):1390-1399 (2000).
Mashhoon, et al., "Crystal structure of a conformation-selective casein kinase-1 inhibitor," J Biol Chem 275(26):20052-20060 (2000).
McMahon, et al., "The essential cofactor TRRAP recruits the histone acetyltransferase hGCN5 to c-Myc," Molecular & Cellular Biology 20(2):556-562 (2000).
Mestdagh, et al., "MYCN/c-MYC-induced microRNAs repress coding gene networks associated with poor outcome in MYCN/c-MYC-activated tumors," Oncogene 29(9):1394-1404 (2010).
Mitani, et al., "Analysis of c-myc DNA amplification in non-small cell lung carcinoma in comparison with small cell lung carcinoma using polymerase chain reaction," Clin Exp Med 1 (2):105-111 (2001).
Nikiforov, et al., "TRRAP-dependent and TRRAP-independent transcriptional activation by Myc family oncoproteins," Mol Cell Biol 22(14):5054-5063 (2002).
Park, at al., "Neuroblastoma: Biology, Prognosis and Treatment," Pediatric Clinics of North America 55 (1), 97-120 (2008).
Ray, et al., "MYC can induce DNA breaks in vivo and in vitro independent of reactive oxygen species," Cancer Res 66(13):6598-6605 (2006).
Regan, et al., "Hsp90 inhibition increases p53 expression and destabilizes MYCN and MYC in neuroblastoma," International Journal of Oncology, 32(1):105-112 (2011).
Riley, et al., "A systematic review of molecular and biological tumor markers in neuroblastoma," Clin Cancer Res 10(1 Pt 1):4-12 (2004).
Robinson, et al., "c-Myc accelerates S-Phase and requires WRN to avoid replication stress," PLoS One 4(6):e5951 (2009).

(56) References Cited

OTHER PUBLICATIONS

Sandrine, et al., "Oncogenic cooperation between H-Twist and N-Myc overrides failsafe programs in cancer cells," Cancer Cell, 6(6):625-630 (2004).
Sato, et aal., "Fluorescence in situ hybridization analysis of c-myc amplification in stage TNM prostate cancer in Japanese patients," Int J Urol 13 (6), 761-766 (2006).
Soucek, et al., "Modelling Myc inhibition as a cancer therapy," Nature 455(7213):679-683 (2008).
Takahashi, et al., "Amplification of c-myc and cyclin D1 genes in primary and metastatic carcinomas of the liver," Pathol Int 57(7):437-442 (2007).
Trumpp, et al., "c-Myc regulates mammalian body size by controlling cell number but not cell size," Nature 414(6865):768-773 (2001).
Wang, et al., "Improved low molecular weight Myc-Max inhibitors," Mol Cancer Ther 6(9):2399-2408 (2007).
Weiss, et al., "Targeted expression of MYCN causes neuroblastoma in transgenic mice," Embo J 16(11):2985-2995 (1997).
Wu, et al., "Increased I-Myc copy number and over-expression of I-Myc were observed in 15% and 40% of EOC, respectively," Am J Pathol, 2003.
Yang, et al., "Inhibition of casein kinase 1-epsilon induces cancer-cell-selective, PERIOD2-dependent growth arrest," Genome Biol 9(6):R92 (2008).
U.S. Appl. No. 14/237,838, filed Feb. 7, 2014, Toyoshima, "Methods and Compositions for Inhibiting the Growth and/or Proliferation of MYC-Driven Tumor Cells."
Aarts et al. "Forced Mitotic Entry of S-Phase Cells as a Therapeutic Strategy Induced by Inhibition of WEE1", *Cancer Discovery* (2012), 2: 524-539. Published Online First Apr. 23, 2012; doi: 10.1158/2159-8290.CD-11-0320.
Agochiya et al. "Increased dosage and amplification of the focal adhesion kinase gene in human cancer cells", *Oncogene* (1999), 18(41): 5646-5653.
Arabi et al. "c-Myc associates with ribosomal DNA and activates RNA polymerase I transcription", *Nat Cell Biol* (2005), 7(3): 303-310.
Barna et al. "Suppression of Myc oncogenic activity by ribosomal protein haploinsufficiency", *Nature* (2008), 456(7224): 971-975.
Bartz et al. "Small interfering RNA screens reveal enhanced cisplatin cytotoxicity in tumor cells having both BRCA network and TP53 disruptions", *Molecular and Cellular Biology* (2006), 26(24): 9377-9386.
Benanti et al. "Epigenetic down-regulation of ARF expression is a selection step in immortalization of human fibroblasts by c-Myc", *Mol Cancer Res* (2007), 5(11): 1181-1189. Published Online First Nov. 2, 2007; doi: 10.1158/1541-7786.MCR-06-0372.
Benanti and Galloway. "Normal human fibroblasts are resistant to RAS-induced senescence", *Molecular and Cellular Biology* (2004), 24(7): 2842-2852.
Berns, et al. "c-myc Amplification Is a Better Prognostic Factor than HER2/neu Amplification in Primary Breast Cancer", *Cancer Res* (1992), 52(5): 1107-1113.
Birmingham et al. "Statistical methods for analysis of high-throughput RNA interference screens", *Nat. Methods.* (2009), 6(8): 569-575.
Blancato et al. "Correlation of amplification and overexpression of the c-myc oncogene in high-grade breast cancer: FISH, in situ hybridisation and immunohistochemical analyses", *British Journal of Cancer* (2004), 90(8): 1612-1619.
Bridges et al. "MK-1775, a Novel Wee1 Kinase Inhibitor, Radiosensitizes p53-Defective Human Tumor Cells", *Clinical Cancer Research* (2011), 17(17): 5638-5648. Published Online First Jul. 28, 2011; doi: 10.1158/1078-0432.CCR-11-0650.
Campaner, et al. "Cdk2 suppresses cellular senescence induced by the c-myc oncogene", *Nat Cell Biol* (2010), 12(1): 54-59 (sup pp. 51-14).
Chung et al. "Median Absolute Deviation to Improve Hit Selection for Genome-Scale RNAi Screens", *Journal of Biomolecular Screening* (2008), 13(2): 149-158.
Cole et al. "RNAi screen of the protein kinome identifies checkpoint kinase 1 (CHK1) as a therapeutic target in neuroblastoma," *Proceedings of the National Academy of Sciences* (2011), 108(8): 3336-3341.
Dar et al. "Aurora Kinase Inhibitors—Rising Stars in Cancer Therapeutics?", *Molecular Cancer Therapy* (2010), 9(2): 268-278. Published Online First Feb. 2, 2010; doi: 10.1158/1535-7163.MCT-09-0765.
De Witt Hamer et al. "WEE1 Kinase Targeting Combined with DNA-Damaging Cancer Therapy Catalyzes Mitotic Catastrophe", *Clinical Cancer Research* (2011), 17: 4200-4207. Published Online First May 11, 2011.
Debnath et al. "rlk/TXK Encodes Two Forms of a Novel Cysteine String Tyrosine Kinase Activated by Src Family Kinases", *Molecular and Cellular Biology* (1999), 19(2): 1498-1507.
Darcy et al. "Prognostic relevance of c-MYC gene amplification and polysomy for chromosome 8 in suboptimally-resected, advanced stage epithelial ovarian cancers: A Gynecologic Oncology Group study", *Gynecologic Oncology* (2009), 114(3): 472-479.
Doles and Hemann. "Nek4 Status Differentially Alters Sensitivity to Distinct Microtubule Poisons", *Cancer Research* (2010), 70: 1033-1041.
Dominguez-Sola et al. "Non-transcriptional control of DNA replication by c-Myc", *Nature* (2007), 448(7152): 445-451.
Egloff and Grandis. "Targeting epidermal growth factor receptor and SRC pathways in head and neck cancer", *Semin Oncol.* (2008), 35(3): 286-297.
EP Patent Application No. 12772551.3, Communication dated Jul. 30, 2015.
Firestein, et al. "CDK8 is a colorectal cancer oncogene that regulates β-catenin activity", *Nature* (2008), 455(7212): 547-551.
Grandori et al. "c-Myc binds to human ribosomal DNA and stimulates transcription of rRNA genes by RNA polymerase I", *Nat. Cell. Biol.* (2005), 7(3): 311-318.
Grandori et al. "Myc-Max heterodimers activate a DEAD box gene and interact with multiple E box-related sites in vivo", *The EMBO Journal* (1996), 15(16): 4344-4357.
Grandori et al. "Werner syndrome protein limits MYC-induced cellular senescence", *Genes & Development* (2003), 17(13): 1569-1574.
Greer and Rubin. "Casein kinase 1 delta functions at the centrosome to mediate Wnt-3a-dependent neurite outgrowth", *J. Cell. Biol.* (2011), 192(6): 993-1004.
Harsha et al. "A Compendium of Potential Biomarkers of Pancreatic Cancer", *PLOS Medicine* (2009), 6(4): e1000046, 1-6.
Hirai et al. "Small-molecule inhibition of Wee1 kinase by MK-1775 selectively sensitizes p53-deficient tumor cells to DNA-damaging agents", *Molecular Cancer Therapeutics* (2009), 8(11): 2992-3000. Published Online First Nov. 3, 2009; doi: 10.1158/1535-7163.MCT-09-0463.
Hopkins and Groom. "The druggable genome", *Nat Rev Drug Discov* (2002), 1(9): 727-730.
Japanese Patent Application No. 2013-503928, Notice of Reasons for Rejection dated Mar. 20, 2015 (with English translation).
Jenkins et al. "Detection of c-myc oncogene amplification and chromosomal anomalies in metastatic prostatic carcinoma by fluorescence in situ hybridization", *Cancer Research* (1997), 57(3): 524-531.
Jones et al. "Core signaling pathways in human pancreatic cancers revealed by global genomic analyses", Science (2008), 321(5897): 1801-1806.
Katayama and Sen. "Aurora kinase inhibitors as anticancer molecules", *Biochim Biophys Acta.* (2010), 1799(10-12): 829-839. doi: 10.1016/j.bbagrm.2010.09.004. Epub Sep. 20, 2010.
Kim et al. "CK1ε is required for breast cancers dependent on β-catenin activity", *PLoS One* (2010), 5(2): e8979, 1-10.
Kiyono et al. "Both Rb/p16$^{INK4a}$ inactivation and telomerase activity are required to immortalize human epithelial cells", *Nature* (1998), 396(6706): 84-88.

(56) References Cited

OTHER PUBLICATIONS

Kozma et al. "Investigation of c-myc oncogene amplification in colorectal cancer", *Cancer Letters* (1994), 81(2): 165-169.

Luoto et al. "Tumor cell kill by c-MYC depletion: role of MYC-regulated genes that control DNA double-strand break repair", Cancer Research (2010), 70(21): 8748-8759. Published Online First Oct. 12, 2010; DOI: 10.1158/0008-5472.CAN-10-0944.

Lutz et al. "Conditional expression of N-myc in human neuroblastoma cells increases expression of α-prothymosin and ornithine decarboxylase and accelerates progression into S-phase early after mitogenic stimulation of quiescent cells," *Oncogene* (1996), 13(4): 803-812.

Ma et al. "Death by releasing the breaks: CHK1 inhibitors as cancer therapeutics", *Trends Mol Med*. (2011), 17(2): 88-96. doi: 10.1016/j.molmed.2010.10.009. Epub Nov. 17, 2010.

Major, et al. "New Regulators of Wnt/β-Catenin Signaling Revealed by Integrative Molecular Screening", *Science Signaling* (2008), 1(45): ra12, 1-11.

Mano et al. "Tec protein-tyrosine kinase is an effector molecule of Lyn protein-tyrosine kinase", *FASEB* (1996), 10: 637-42.

McMahon et al. "The essential cofactor TRRAP recruits the histone acetyltransferase hGCN5 to c-Myc", *Molecular & Cellular Biology* (2000), 20(2): 556-562.

Mitani et al. "Analysis of c-myc DNA amplification in non-small cell lung carcinoma in comparison with small cell lung carcinoma using polymerase chain reaction", *Clin Exp Med* (2001), 1(2): 105-111.

Moniz et al. "Nek family of kinases in cell cycle, checkpoint control and cancer", *Cell Division* (2011) 6: 18, 10 pages.

Moses et al., "Intended transcriptional silencing with siRNA results in gene repression through sequence-specific off-targeting", RNA (2010), 16: 430-441. Published in Advance Dec. 21, 2009, doi: 10.1261/rna.1808510.

Nguyen et al. "Nek4 regulates entry into replicative senescence and the response to DNA damage in human fibroblasts", *Molecular and Cellular Biology* (2012), 32: 3963-3977.

Nikiforov et al. "TRRAP-Dependent and TRRAP-Independent Transcriptional Activation by Myc Family Oncoproteins", *Molecular and Cellular Biology* (2002), 22(14): 5054-5063.

PCT/US2012/050186, International Search Report, dated Apr. 18, 2013.

PCT/US2012/050186, Written Opinion of the International Searching Authority, dated Apr. 18, 2013.

PCT/US2012/050186, International Preliminary Report on Patentability, dated Feb. 11, 2014.

PCT/US2014/066884, International Search Report, dated Apr. 30, 2015.

PCT/US2014/066884, Written Opinion of the International Searching Authority, dated Apr. 30, 2015.

Poeta et al. "TP53 Mutations and Survival in Squamous-Cell Carcinoma of the Head and Neck", *N Engl J Med*. (2007), 357(25): 2552-2561.

Rajeshkumar et al. "MK-1775, a Potent Wee1 Inhibitor, Synergizes with Gemcitabine to Achieve Tumor Regressions, Selectively in p53-Deficient Pancreatic Cancer Xenografts", *Clinical Cancer Research* (2011), 17: 2799-2806. Published Online First Mar. 9, 2011; doi: 10.1158/1078-0432.CCR-10-2580.

Ray, et al. "MYC Can Induce DNA Breaks In vivo and In vitro Independent of Reactive Oxygen Species", *Cancer Research* (2006), 66(13): 6598-6605.

Regan et al. "Hsp90 inhibition increases p53 expression and destabilizes MYCN and MYC in neuroblastoma", *International Journal of Oncology* (2011), 32(1): 105-112.

Robinson, et al. "c-Myc Accelerates S-Phase and Requires WRN to Avoid Replication Stress", PLoS One (2009), 4(6): e5951, 1-10.

Sato et al. "Fluorescence in situ hybridization analysis of c-myc amplification in stage $T_3N_0M_0$ prostate cancer in Japanese patients", *International Journal of Urology* (2006), 13(6): 761-766.

Soucek et al. "Modelling Myc inhibition as a cancer therapy", *Nature* (2008), 455(7213): 679-683.

Stabile et al. "c-Src Activation Mediates Erlotinib Resistance in Head and Neck Cancer by Stimulating c-Met", *Clinical Cancer Research* (2013), 19(2): 380-392. Published Online First, Dec. 4, 2012. doi: 10.1158/1078-0432.CCR-12-1555.

Takahashi et al. "Amplification of c-myc and cyclin D1 genes in primary and metastatic carcinomas of the liver", *Pathology International* (2007), 57(7): 437-442.

Trumpp et al. "c-Myc regulates mammalian body size by controlling cell number but not cell size", *Nature* (2001), 414(6865): 768-773.

U.S. Appl. No. 14/237,838, Office Action dated Mar. 11, 2015.

Valsesia-Wittmann et al., "Oncogenic cooperation between H-Twist and N-Myc overrides failsafe programs in cancer cells", *Cancer Cell*, 6(6): 625-630 (2004).

Van Linden et al. "Inhibition of Wee1 Sensitizes Cancer Cells to Antimetabolite Chemotherapeutics In Vitro and In Vivo, Independent of p53 Functionality", *Molecular Cancer Therapy* (2013), 12: 2675-2684. Published Online First Oct. 11, 2013; doi: 10.1158/1535-7163.MCT-13-0424.

Wang et al. "Improved low molecular weight Myc-Max inhibitors", *Molecular Cancer Therapy* (2007), 6(9): 2399-2408.

Wang et al. "Increased radio-resistance and accelerated B cell lymphomas in mice with Mdmx mutations that prevent modifications by DNA-damage-activated kinases", *Cancer Cell* (2009), 16(1): 33-43.

Weber et al. "Retinoic acid-mediated growth inhibition of small cell lung cancer cells is associated with reduced myc and increased $p27^{Kip1}$ Expression", International Journal of Cancer (1999), 80(6): 935-943.

Wen et al. "Knockdown of p21-activated Kinase 6 Inhibits Prostate Cancer Growth and Enhances Chemosensitivity to Docetaxel", Urology (2009), 73(6): 1407-1411.

Wheeler et al. "Lyn Kinase Mediates Cell Motility and Tumor Growth in EGFRvIII-Expressing Head and Neck Cancer", *Clinical Cancer Research* (2012), 18: 2850-2860. Published Online First Apr. 6, 2012; doi: 10.1158/1078-0432.CCR-11-2486.

Wu et al. "Amplification and Overexpression of the L-MYC Proto-Oncogene in Ovarian Carcinomas", *American Journal of Pathology* (2003), 162(5): 1603-1610.

Xi et al. "Src kinases mediate STAT growth pathways in squamous cell carcinoma of the head and neck", *J Biol Chem*. (2003), 278(34): 31574-31583. First Published Online May 27, 2003, doi: 10.1074/jbc.M303499200.

Xu et al. "Integrative analysis of DNA copy number and gene expression in metastatic oral squamous cell carcinoma identifies genes associated with poor survival", *Molecular Cancer* (2010), 9: 143, 12 pages.

Xu et al. "Integrative genomics in combination with RNA interference identifies prognostic and functionally relevant gene targets for oral squamous cell carcinoma", *PLOS Genetics* (2013), 9(1): e1003169. doi: 10.1371/journal.pgen.1003169.

Zhang et al. "A Simple Statistical Parameter for Use in Evaluation and Validation of High Throughput Screening Assays", *Journal of Biomolecular Screening* (1999), 4(2): 67-73.

Zhang et al. "SRC family kinases mediate epidermal growth factor receptor ligand cleavage, proliferation, and invasion of head and neck cancer cells", *Cancer Research* (2004), 64: 6166-6173.

Chen, Ch, et al., "Overexpression of Cyclin D1 and c-Myc Gene Products in Human Primary Epithelial Ovarian Cancer," Int. J. Gynecol. Cnacer, Sep.-Oct. 2005; 15(5): 878-83.

International Search Report for International Application No. PCT/US2011/031460, dated Dec. 20, 2011.

Written Opinion for International Application No. PCT/US2011/031460, dated Dec. 20, 2011.

International Preliminary Report on Patentability for International Application No. PCT/US2011/031460, dated Oct. 9, 2012.

Biechele et al., "Transcription-Based Reporters of Wnt/beta-Catenin Signaling," *Cold Spring Harb Protoc*, doi:10.1101/pdb.prot5223 (2009).

Boon et al., "N-myc Enhances the Expression of a Large Set of Genes Functioning in Ribosome Biogenesis and Protein Synthesis," *The Embo Journal*, 20(6):1383-1393 (2001).

(56) References Cited

OTHER PUBLICATIONS

Cheong et al. "IC261 induces cell cycle arrest and apoptosis of human cancer cells via CK1δ/ε and Wnt/β-catenin independent inhibition of mitotic spindle formation" *Oncogene*, 30:2558-2569 (2011).
Cowling et al., "Turning the Tables: Myc Activates Wnt in Breast Cancer," *Cell Cycle*, 6(21):2625-2627 (2007).
Fuja et al., "Somatic Mutations and Altered Expressions of the Candidate Tumor Suppressors CSNK1ε, DLG1, and EDD/hHYD in Mammary Ductal Carcinoma", *Cancer Research*, 64:942-951 (2004).
Hanks et al., "The eukaryotic protein kinase superfamily: kinase (catalytic domain structure and classification," *The FASEB Journal*, 9:576-596 (1995).
Hanson et al., "Effects of c-myc Expression on Cell Cycle Progression," *Molecular and Cellular Biology*, 14(9):5748-5755 (1994).
Malynn et al., "N-myc Can Functionally Replace c-myc in Murine Development, Cellular Growth, and Differentiation," *Genes & Development* 14:1390-1399 (2000).
Marcu et al., "myc function and regulation," *Ann. Rev. Biochem.*, 61:809-860 (1992).
Mashhoon et al., "Crystal Structure of a Conformation-Selective Casein Kinase-1 Inhibitor," *The Journal of Biological Chemistry*, 275(26):20052-20060 (2000).
Mestdagh et al., "MYCN/c-MYC-Induced microRNAs Repress Coding Gene Networks Associated with Poor Outcome in MYCN/c-MYC-Activated Tumors," *Oncogene*, 29:1394-1404 (2010).
Park et al., "Neuroblastoma: Biology, Prognosis and Treatment," *Pediatric Clinics of North America*, 55:97-120, 2008.
Riley et al., "A Systematic Review of Molecular and Biological Tumor Markers in Neuroblastoma," *Clinical Cancer Research*, 10:4-12 (2004).
Sasaki et al., "A binding site for Gli proteins is essential for HNF-3β floor plate enhancer activity in transgenics and can respond to Shh in vitro," *Development*, 124:1313-1322 (1997).
Sakanaka, "Phosphorylation and Regulation of Beta-Catenin by Casein Kinase I Epsilon," *J Biochem*, 132:697-703 (2002).
Toyoshima et al. "Functional genomics identifies therapeutic targets for MYC-driven Cancer" *PNAS*, 109(24):9545-9550 (2012).
Weiss et al., "Targeted Expression of MYCN Causes Neuroblastoma in Transgenic Mice," *The EMBO Journal*, 16(11):2985-2995 (1997).
Yang et al., "Inhibition of casein kinase 1-epsilon induces cancer-cell-selective, PERIOD2-dependent growth arrest," *Genome Biology*, 9(6) R92:1-13 (2008).
Zhou et al., "Overexpression of Cyclin D1 Enhances Gene Amplification," *Cancer Research*, 56:36-39 (1996).
Annibali, Daniela, et al. "Myc inhibition is effective against glioma and reveals a role for Myc in proficient mitosis." Nature Communications (2014); 5: 4632, 11 pages.
Armstrong, Stephen R., et al. "Distinct genetic alterations occur in ovarian tumor cells selected for combined resistance to carboplatin and docetaxel." Journal of Ovarian Research (2012); 5.1: 1-20.
Cai, Guoqing, et al. "Phosphorylation of glycogen synthase kinase-3 β at serine 9 confers cisplatin resistance in ovarian cancer cells." International Journal of Oncology (2007); 31.3: 657-662.
Cermelli, Silvia, et al. "Synthetic lethal screens as a means to understand and treat MYC-driven cancers." Cold Spring Harbor Perspectives in Medicine (2014); 4.3 : a014209.
Cowling, Victoria H., et al. "c-Myc transforms human mammary epithelial cells through repression of the Wnt inhibitors DKK1 and SFRP1." Molecular and Cellular Biology (2007); 27.14: 5135-5146.
Haque, Azizul, et al. "Induction of apoptosis and immune response by all-trans retinoic acid plus interferon-gamma in human malignant glioblastoma T98G and U87MG cells." Cancer Immunology, Immunotherapy (2007); 56.5: 615-625.
Haque, Azizul, et al. "Emerging role of combination of all-trans retinoic acid and interferon-gamma as chemoimmunotherapy in the management of human glioblastoma." Neurochemical Research (2007); 32.12: 2203-2209.
Hirvonen, H. E., et al. "Differential expression of myc, max and RB1 genes in human gliomas and glioma cell lines." British journal of cancer 69.1 (1994): 16.
Iorns, Elizabeth, et al. "CRK7 modifies the MAPK pathway and influences the response to endocrine therapy." Carcinogenesis (2009); 30.10: 1696-1701.
Li, Chi-Ming, et al. "PEG10 is a c-MYC target gene in cancer cells." Cancer Research (2006); 66.2: 665-672.
The Merck Manual, 18th edition, Japanese ver., 2005, [online], Retrieved from the internet:, with English summary/translation, 3 pages <URL:http://merckmanual.jp/mmpej/sec19/ch285/ch285b.html>.
Popadiuk, Cathy M., et al. "Antisense suppression of pygopus2 results in growth arrest of epithelial ovarian cancer." Clinical Cancer Research (2006); 12.7: 2216-2223.
Swiatek, Wojciech, et al. "Regulation of casein kinase Iε activity by Wnt signaling." Journal of Biological Chemistry (2004); 279.13: 13011-13017.
U.S. Appl. No. 15/000,933, Office Action dated Nov. 30, 2016, 16 pages.
Wada, Randal K., et al. "Interferon-γ and retinoic acid down-regulate N-myc in neuroblastoma through complementary mechanisms of action." Cancer Letters (1997); 121.2: 181-188.
Wang, Yi-hua, et al. "Knockdown of c-Myc expression by RNAi inhibits MCF-7 breast tumor cells growth in vitro and in vivo." Breast Cancer Research 7.2 (2004): 1.
Wright, Kim, et al. "β-Catenin mutation and expression analysis in ovarian cancer: Exon 3 mutations and nuclear translocation in 16% of endometrioid tumours." International Journal of Cancer (1999); 82.5: 625-629.
Rinsho Yakuri, Clinical Pharmacology, Mar. 2010, vol. 41, No. 2, p. 23S-24S (with English summary/translation of pertinent portions).
EP Patent Application No. 11766677.6, EPO Communication dated Feb. 5, 2016.
EP Patent Application No. 12772551.3, EPO Communication dated Jul. 30, 2015.
EP Patent Application No. 12772551.3, EPO Communication dated Jun. 21, 2016.
Japanese Patent Application No. 2013-503928, Notice of Reasons for Rejection dated Feb. 29, 2016 (with English translation).
Li et al., "Down-regulation of pescadillo inhibits proliferation and tumorigenicity of breast cancer cells", Cancer Science (2009), 100(12): 2255-2260.
PCT/US2014/066884, International Preliminary Report on Patentability, dated Jun. 2, 2016.
Walton, K., et al., "Selective Inhibition of Casein Kinase IE Minimally Alters Circadian Clock Period," The Journal of Pharmacology and Experimental Therapeutics, (2009) vol. 330, No. 2, pp. 430-439.

\* cited by examiner

IC-261

↓ DMSO

SEQUENCE LISTING

```
<160> NUMBER OF SEQ ID NOS: 4

<210> SEQ ID NO 1
<211> LENGTH: 1251
<212> TYPE: DNA
<213> ORGANISM: Homo sapiens
<220> FEATURE:
<221> NAME/KEY: CDS
<222> LOCATION: (1)..(1251)

<400> SEQUENCE: 1 atg gag cta cgt gtg ggg aac aag tac cgc ctg gga cgg aag atc ggg    48
Met Glu Leu Arg Val Gly Asn Lys Tyr Arg Leu Gly Arg Lys Ile Gly
1               5                   10                  15 agc ggg tcc ttc gga gat atc tac ctg ggt gcc aac atc gcc tct ggt    96
Ser Gly Ser Phe Gly Asp Ile Tyr Leu Gly Ala Asn Ile Ala Ser Gly
            20                  25                  30 gag gaa gtc gcc atc aag ctg gag tgt gtg aag aca aag cac ccc cag   144
Glu Glu Val Ala Ile Lys Leu Glu Cys Val Lys Thr Lys His Pro Gln
        35                  40                  45 ctg cac atc gag agc aag ttc tac aag atg atg cag ggt ggc gtg ggg   192
Leu His Ile Glu Ser Lys Phe Tyr Lys Met Met Gln Gly Gly Val Gly
    50                  55                  60 atc ccg tcc atc aag tgg tgc gga gct gag ggc gac tac aac gtg atg   240
Ile Pro Ser Ile Lys Trp Cys Gly Ala Glu Gly Asp Tyr Asn Val Met
65                  70                  75                  80 gtc atg gag ctg ctg ggg cct agc ctc gag gac ctg ttc aac ttc tgt   288
Val Met Glu Leu Leu Gly Pro Ser Leu Glu Asp Leu Phe Asn Phe Cys
                85                  90                  95 tcc cgc aaa ttc agc ctc aag acg gtg ctc ctc ttg gcc gac cag atg   336
Ser Arg Lys Phe Ser Leu Lys Thr Val Leu Leu Leu Ala Asp Gln Met
            100                 105                 110 atc agc cgc atc gag tat atc cac tcc aag aac ttc atc cac cgg gac   384
Ile Ser Arg Ile Glu Tyr Ile His Ser Lys Asn Phe Ile His Arg Asp
        115                 120                 125 gtc aag ccc gac aac ttc ctc atg ggg ctg ggg aag aag ggc aac ctg   432
Val Lys Pro Asp Asn Phe Leu Met Gly Leu Gly Lys Lys Gly Asn Leu
    130                 135                 140 gtc tac atc atc gac ttc ggc ctg gcc aag aag tac cgg gac gcc cgc   480
Val Tyr Ile Ile Asp Phe Gly Leu Ala Lys Lys Tyr Arg Asp Ala Arg
145                 150                 155                 160 acc cac cag cac att ccc tac cgg gaa aac aag aac ctg acc ggc acg   528
Thr His Gln His Ile Pro Tyr Arg Glu Asn Lys Asn Leu Thr Gly Thr
                165                 170                 175 gcc cgc tac gct tcc atc aac acg cac ctg ggc att gag caa agc cgt   576
Ala Arg Tyr Ala Ser Ile Asn Thr His Leu Gly Ile Glu Gln Ser Arg
            180                 185                 190 cga gat gac ctg gag agc ctg ggc tac gtg ctc atg tac ttc aac ctg   624
Arg Asp Asp Leu Glu Ser Leu Gly Tyr Val Leu Met Tyr Phe Asn Leu
        195                 200                 205 ggc tcc ctg ccc tgg cag ggg ctc aaa gca gcc acc aag cgc cag aag   672
Gly Ser Leu Pro Trp Gln Gly Leu Lys Ala Ala Thr Lys Arg Gln Lys
    210                 215                 220
```

```
tat gaa cgg atc agc gag aag aag atg tca acg ccc atc gag gtc ctc    720
Tyr Glu Arg Ile Ser Glu Lys Lys Met Ser Thr Pro Ile Glu Val Leu
225                 230                 235                 240 tgc aaa ggc tat ccc tcc gaa ttc tca aca tac ctc aac ttc tgc cgc    768
Cys Lys Gly Tyr Pro Ser Glu Phe Ser Thr Tyr Leu Asn Phe Cys Arg
                245                 250                 255 tcc ctg cgg ttt gac gac aag ccc gac tac tct tac cta cgt cag ctc    816
Ser Leu Arg Phe Asp Asp Lys Pro Asp Tyr Ser Tyr Leu Arg Gln Leu
            260                 265                 270 ttc cgc aac ctc ttc cac cgg cag ggc ttc tcc tat gac tac gtc ttt    864
Phe Arg Asn Leu Phe His Arg Gln Gly Phe Ser Tyr Asp Tyr Val Phe
        275                 280                 285 gac tgg aac atg ctg aaa ttc ggt gca gcc cgg aat ccc gag gat gtg    912
Asp Trp Asn Met Leu Lys Phe Gly Ala Ala Arg Asn Pro Glu Asp Val
    290                 295                 300 gac cgg gag cgg cga gaa cac gaa cgc gag gag agg atg ggg cag cta    960
Asp Arg Glu Arg Arg Glu His Glu Arg Glu Glu Arg Met Gly Gln Leu
305                 310                 315                 320 cgg ggg tcc gcg acc cga gcc ctg ccc cct ggc cca ccc acg ggg gcc   1008
Arg Gly Ser Ala Thr Arg Ala Leu Pro Pro Gly Pro Pro Thr Gly Ala
                325                 330                 335 act gcc aac cgg ctc cgc agt gcc gcc gag ccc gtg gct tcc acg cca   1056
Thr Ala Asn Arg Leu Arg Ser Ala Ala Glu Pro Val Ala Ser Thr Pro
            340                 345                 350 gcc tcc cgc atc cag ccg gct ggc aat act tct ccc aga gcg atc tcg   1104
Ala Ser Arg Ile Gln Pro Ala Gly Asn Thr Ser Pro Arg Ala Ile Ser
        355                 360                 365 cgg gtc gac cgg gag agg aag gtg agt atg agg ctg cac agg ggt gcg   1152
Arg Val Asp Arg Glu Arg Lys Val Ser Met Arg Leu His Arg Gly Ala
    370                 375                 380 ccc gcc aac gtc tcc tcc tca gac ctc act ggg cgg caa gag gtc tcc   1200
Pro Ala Asn Val Ser Ser Ser Asp Leu Thr Gly Arg Gln Glu Val Ser
385                 390                 395                 400 cgg atc cca gcc tca cag aca agt gtg cca ttt gac cat ctc ggg aag   1248
Arg Ile Pro Ala Ser Gln Thr Ser Val Pro Phe Asp His Leu Gly Lys
                405                 410                 415 tga                                                               1251

<210> SEQ ID NO 2
<211> LENGTH: 416
<212> TYPE: PRT
<213> ORGANISM: Homo sapiens

<400> SEQUENCE: 2

Met Glu Leu Arg Val Gly Asn Lys Tyr Arg Leu Gly Arg Lys Ile Gly
1               5                   10                  15

Ser Gly Ser Phe Gly Asp Ile Tyr Leu Gly Ala Asn Ile Ala Ser Gly
            20                  25                  30

Glu Glu Val Ala Ile Lys Leu Glu Cys Val Lys Thr Lys His Pro Gln
        35                  40                  45

Leu His Ile Glu Ser Lys Phe Tyr Lys Met Met Gln Gly Gly Val Gly
    50                  55                  60

Ile Pro Ser Ile Lys Trp Cys Gly Ala Glu Gly Asp Tyr Asn Val Met
65                  70                  75                  80

Val Met Glu Leu Leu Gly Pro Ser Leu Glu Asp Leu Phe Asn Phe Cys
                85                  90                  95

Ser Arg Lys Phe Ser Leu Lys Thr Val Leu Leu Leu Ala Asp Gln Met
            100                 105                 110
```

```
Ile Ser Arg Ile Glu Tyr Ile His Ser Lys Asn Phe Ile His Arg Asp
        115                 120                 125

Val Lys Pro Asp Asn Phe Leu Met Gly Leu Gly Lys Gly Asn Leu
130                 135                 140

Val Tyr Ile Ile Asp Phe Gly Leu Ala Lys Lys Tyr Arg Asp Ala Arg
145                 150                 155                 160

Thr His Gln His Ile Pro Tyr Arg Glu Asn Lys Asn Leu Thr Gly Thr
                165                 170                 175

Ala Arg Tyr Ala Ser Ile Asn Thr His Leu Gly Ile Glu Gln Ser Arg
                180                 185                 190

Arg Asp Asp Leu Glu Ser Leu Gly Tyr Val Leu Met Tyr Phe Asn Leu
            195                 200                 205

Gly Ser Leu Pro Trp Gln Gly Leu Lys Ala Ala Thr Lys Arg Gln Lys
210                 215                 220

Tyr Glu Arg Ile Ser Glu Lys Lys Met Ser Thr Pro Ile Glu Val Leu
225                 230                 235                 240

Cys Lys Gly Tyr Pro Ser Glu Phe Ser Thr Tyr Leu Asn Phe Cys Arg
                245                 250                 255

Ser Leu Arg Phe Asp Asp Lys Pro Asp Tyr Ser Tyr Leu Arg Gln Leu
                260                 265                 270

Phe Arg Asn Leu Phe His Arg Gln Gly Phe Ser Tyr Asp Tyr Val Phe
            275                 280                 285

Asp Trp Asn Met Leu Lys Phe Gly Ala Ala Arg Asn Pro Glu Asp Val
            290                 295                 300

Asp Arg Glu Arg Arg Glu His Glu Arg Glu Glu Arg Met Gly Gln Leu
305                 310                 315                 320

Arg Gly Ser Ala Thr Arg Ala Leu Pro Pro Gly Pro Thr Gly Ala
                325                 330                 335

Thr Ala Asn Arg Leu Arg Ser Ala Ala Glu Pro Val Ala Ser Thr Pro
                340                 345                 350

Ala Ser Arg Ile Gln Pro Ala Gly Asn Thr Ser Pro Arg Ala Ile Ser
                355                 360                 365

Arg Val Asp Arg Glu Arg Lys Val Ser Met Arg Leu His Arg Gly Ala
370                 375                 380

Pro Ala Asn Val Ser Ser Ser Asp Leu Thr Gly Arg Gln Glu Val Ser
385                 390                 395                 400

Arg Ile Pro Ala Ser Gln Thr Ser Val Pro Phe Asp His Leu Gly Lys
                405                 410                 415

<210> SEQ ID NO 3
<211> LENGTH: 19
<212> TYPE: DNA
<213> ORGANISM: Artificial Sequence
<220> FEATURE:
<223> OTHER INFORMATION: Synthetic

<400> SEQUENCE: 3
ggctatccct ccgaattct                                                  19

<210> SEQ ID NO 4
<211> LENGTH: 19
<212> TYPE: DNA
<213> ORGANISM: Artificial Sequence
<220> FEATURE:
<223> OTHER INFORMATION: Synthetic
```

```
<400> SEQUENCE: 4
gaacggatca gcgagaaga                                              19
```

METHODS FOR IDENTIFYING AND USING INHIBITORS OF CASEIN KINASE 1 EPSILON ISOFORM FOR INHIBITING THE GROWTH AND/OR PROLIFERATION OF MYC-DRIVEN TUMOR CELLS

RELATED APPLICATIONS

This application claims benefit under 35 U.S.C. §119(e) of U.S. Provisional Application No. 61/321,414, filed Apr. 6, 2010, which is herein incorporated by reference in its entirety.

STATEMENT OF GOVERNMENT LICENSE RIGHTS

This invention was made with U.S. Government support under grant number AG026661 awarded by the National Institutes of Health. The U.S. Government has certain rights in this invention.

FIELD OF THE INVENTION

The invention generally relates to methods for identifying and using anticancer therapeutic agents and, more particularly, to methods for identifying inhibitors of casein kinase 1ε-isoform (CSNK1ε) for inhibiting the growth and/or proliferation of MYC-driven tumor cells.

BACKGROUND OF THE INVENTION

Cancer, namely the uncontrolled proliferation of cells, remains a significant health problem worldwide. Although significant advances have been made in the detection and therapy of various cancers, no universally successful method for prevention or treatment is currently available. Current therapies are generally based on a combination of chemotherapy, surgery, or radiation to selectively destroy or remove the proliferating cells. However, these treatments often prove to be inadequate in many patients. Consequently, recent emphasis has focused on personalized treatment of the cellular and genetic causes of specific cancers.

Cancer is the result of the accumulation of multiple genetic mutations, which result in the activation of oncogenes and/or the inactivation of tumor associated suppressor genes. It is the differential expression of these critical genes and their downstream effectors that enables cells to override the controls on the cell cycle and to initiate unchecked proliferation. Although many genetic mechanisms underlying carcinogenesis have been elucidated, the products of many known oncogenes promote essential functions in healthy cells, such as promotion of the cell cycle and cell growth. Thus, many oncogenes and/or oncoproteins are problematic targets for directed cancer treatment because of the toxicity resulting in normal cells. Therefore, there remains a need to identify drug targets associated with oncogene function, wherein treatment of the targets has minimal negative effect on healthy cells.

SUMMARY OF THE INVENTION

This summary is provided to introduce a selection of concepts in a simplified form that are further described below in the Detailed Description. This summary is not intended to identify key features of the claimed subject matter nor is it intended to be used as an aid in determining the scope of the claimed subject matter.

In one aspect, the invention provides a method for inhibiting the growth and/or proliferation of a myc-driven tumor cell comprising the step of contacting the tumor cells with a CSNK1ε inhibitor.

In another aspect, the invention provides a method of treating a subject suffering from a tumor comprising myc-driven tumor cells, comprising administering to the subject an amount of a composition comprising a CSNK1ε inhibitor effective to inhibit the growth and/or proliferation of the tumor cells.

In another aspect, the invention provides a method for identifying compounds capable of inhibiting proliferation of a myc-driven cancer cell. The method according to this aspect of the invention comprises: (a) contacting a myc-driven cancer cell line expressing CSNK1ε with a candidate compound in cell culture; and (b) determining at least one of: (i) the level of WNT expression or activity in the presence and absence of the candidate compound, or (ii) the level of SHH expression or activity in the presence and absence of the candidate compound, or (iii) the level of CSNK1ε expression or activity in the presence and absence of the candidate compound, wherein a decrease in the expression level or activity of WNT; and/or a decrease in the expression level or activity of SHH, and/or a decrease in the expression level or activity of CSNK1ε in the presence of the candidate compound is indicative of a compound that inhibits proliferation of a cancer cell.

DESCRIPTION OF THE DRAWINGS

The foregoing aspects and many of the attendant advantages of this invention will become more readily appreciated as the same become better understood by reference to the following detailed description, when taken in conjunction with the accompanying drawings.

DETAILED DESCRIPTION

Figure 1A:
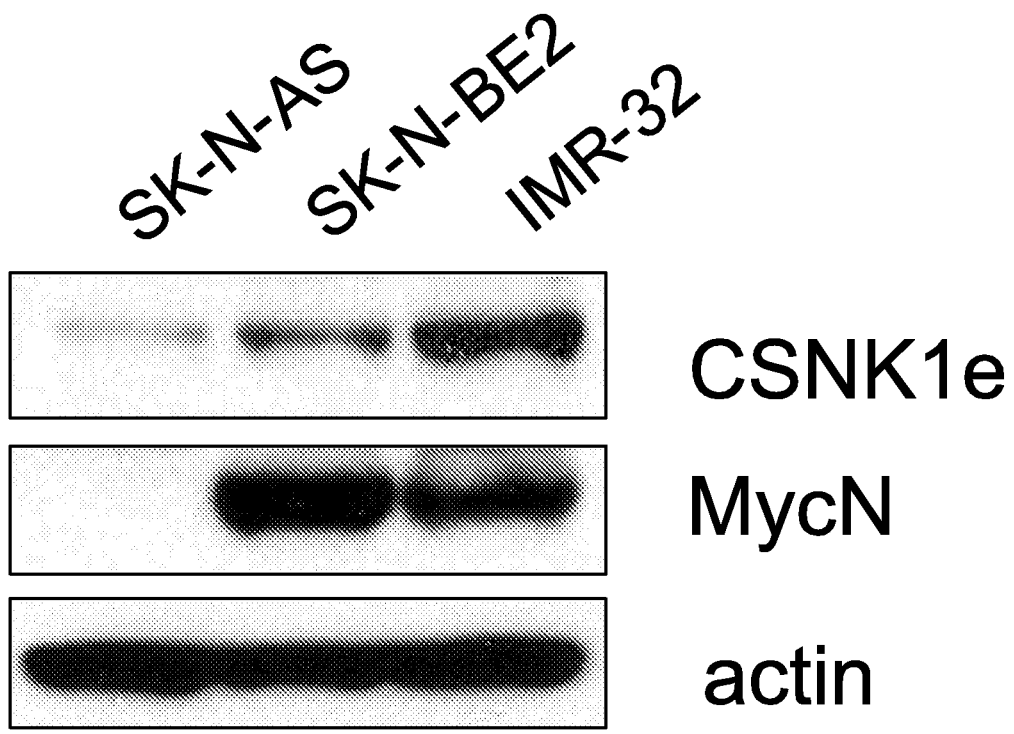
FIG. 1A is a Western Blot illustrating the protein levels of CSNK1ε in neuroblastoma cells with or without amplified MYCN expression; as described in Example 1.

Unless defined otherwise, all technical and scientific terms used herein have the meaning commonly understood by one of ordinary skill in the art to which this invention belongs. Practitioners are particularly directed to Sambrook et al., *Molecular Cloning: A Laboratory Manual*, 2d ed., Cold Spring Harbor Press, Plainsview, N.Y. (1989); and Ausubel et al., *Current Protocols in Molecular Biology* (Supplement 47), John Wiley & Sons, New York (1999), for definitions and terms of the art.

It is contemplated that any embodiment discussed in this specification can be implemented with respect to any method, reagent, or composition of the invention, and vice versa. Furthermore, compositions of the invention can be used to achieve methods of the invention.

As used herein, an "effective amount" or "therapeutically effective amount" of a CSNK1ε inhibitor, or a composition comprising a CSNK1ε inhibitor is an amount sufficient to produce the desired effect, e.g., inhibition of expression or enzymatic (kinase) activity of CSNK1ε in comparison to the normal expression level detected in the absence of the agent, or inhibition of the growth and/or proliferation of a tumor cell. Inhibition of expression or activity of CSNK1ε by an inhibitory agent is achieved when the expression level of the CSNK1ε or protein is about 80%, 70%, 60%, 50%, 40%, 30%, 25%, 20%, 15%, 10%, 5%, or 0% relative to the expression level of the target gene mRNA or protein of a control sample, or when the activity level of the CSNK1ε is about 80%, 70%, 60%, 50%, 40%, 30%, 25%, 20%, 15%, 10%, 5%, or 0% relative to the activity level of CSNK1ε in a control sample without the inhibitory agent.

As used herein, the term to "inhibit the growth and/or proliferation of a tumor cell" means to kill the cell, or permanently or temporarily arrest the growth of the cell. Inhibition of a mammalian tumor cell can be inferred if the number of such cells, either in an in vitro culture vessel, or in a subject, remains constant or decreases after administration of the compositions of the invention. An inhibition of tumor cell proliferation can also be inferred if the absolute number of such cells increases, but the rate of tumor growth decreases.

As used herein, "subject" refers to an organism or to a cell sample, tissue sample or organ sample derived therefrom, including, for example, cultured cell lines, biopsy, blood sample, or fluid sample containing a cell. For example, an organism may be an animal, including but not limited to, an animal such as a cow, a pig, a mouse, a rat, a chicken, a cat, a dog, etc., and is usually a mammal, such as a human.

As used herein, the term "Myc-driven tumor cell(s)" refers to a tumor cell(s) which has a genetic alteration which causes Myc overexpression, (c-Myc, MYCN, or LMYC), such as a genetic alteration which causes Myc overexpression as result of gene duplication, gene amplification, translocation, deregulated transcription leading to overexpression, or aberrant protein regulation. Examples of known genetic alterations which affect such dysregulation include a t8; 14 translocation, genetic amplification of c-Myc or other MYC-family member, and mutations in APC. Examples of Myc-driven tumor cells include Burkitts' Lymphoma cells, neuroblastoma cells, ovarian cancer cells, colon cancer cells, lung cancer cells, breast cancer cells, liver cancer cells, and others as shown in TABLE 1.

c-Myc is a key regulator of growth, proliferation, differentiation and development. Deregulation of the c-Myc oncoprotein has been reported in apoptosis, transformation, and in malignancies of lymphoid and non-lymphoid origin. The c-Myc gene encodes a transcription factor of the helix-loop-helix leucine zipper class and plays a role in the modulation and initiation of transcription. C-Myc binds to E-boxes (CACGTG) in the vicinity of target genes, which are then activated. The DNA binding activity requires dimerization with another helix-loop-helix leucine zipper protein called Max. Max can also interact with transcriptional repressors such as Mad and Mxi1, which presumably down-regulate expression of c-Myc target genes. c-Myc is a short-lived nuclear oncoprotein, which is strictly regulated during the cell cycle of normal diploid cells. Increased half life of the protein is associated with immortalization and transformation. The deregulation of c-Myc is a common feature in many tumors, where it frequently is translocated and/or amplified and overexpressed. In addition, the c-myc gene is often the site of proviral insertion. See Marcu, et al., *Cancer Research* 56:36-39 (1992); Stanton et al., *Mol. Cell. Biol.* 14:5748-5755 (1983); and Cole et al., *Ann. Rev. Biochem.* 61:809 (1986).

N-Myc proto-oncogene protein, or MYCN or NMYC, is a protein encoded by the MYCN gene. As used herein, the terms "n-MYC", "MYCN" and "NMYC" are synonyms and interchangeable. The gene is a member of the MYC family of transcription factors. The expressed protein contains a basic helix-loop-helix domain and must dimerize with another basic helix-loop-helix domain to bind DNA. Like c-Myc, the MYCN protein interacts with MAX. Amplification of the MYCN gene is mostly associated with a variety of tumors, most notably neuroblastomas.

The CSNK1 protein kinase family is evolutionarily conserved with seven mammalian isoforms: α, β, γ1, γ2, γ3, δ and ε. The human CSNK1ε protein (Genbank ref no. CAG30315.1) is set forth as SEQ ID NO:2, encoded by the cDNA (Genbank ref no. CR456429.1) set forth as SEQ ID NO:1. The terms casein kinase 1 epsilon, CSNK1 epsilon, CSNK1ε, and CSNK1e are used interchangeably herein. The gene product of CSNK1ε is known to regulate circadian rhythms by phosphorylating other clock proteins, such as PERIOD. Over expression of CSNK1ε mimics WNT-signaling through phosphorylation of Tcf3 and stabilization of β-catenin, suggesting a functional role in stem cell properties. Additionally, the CSNK1ε protein phosphorylates p53 and prevents it from interaction with Mdm2. CSNK1ε is predominantly expressed in the neural system.

The present invention is based in part on the discovery that the ε-isoform of casein kinase 1 (CSNK1ε) is upregulated in various Myc-driven cancers, and that inhibitors of CSNK1ε are effective in inhibiting the growth and/or proliferation of myc-driven cancer cells and reduce the size of established tumors, but do not adversely affect normally proliferating cells (i.e. not Myc-driven). As described below in Example 1, CSNK1ε expression was found to be elevated in neuroblastoma cells with amplified MYCN expression. Upon knockdown of CSNK1ε expression or chemical inhibition of CSNK1ε kinase activity, neuroblastoma cells with amplified MYCN expression exhibited a loss of viability and reduced proliferation. These results were replicated in vivo in a mouse xenograft model, as described in Example 2. First, xenograft neuroblastoma tumors containing inducible shRNAs targeting CSNK1ε exhibited a reduction in size upon induced knockdown of CSNK1ε expression. Second, administration of CSNK1ε small molecule inhibitor IC261 to mice with xenograft neuroblastoma tumors (with amplified MYCN expression) resulted in reduced tumor sizes. As further described herein, roles were discovered for WNT and SHH signaling in mediating the effect of CSNK1ε on tumor proliferation in neuroblastoma cells with amplified MYCN expression. A similar role for CSNK1ε expression was found in ovarian cancer cells with amplified c-MYC expression. As described in Example 4, ovarian cancer lines with amplified c-MYC expression also exhibited a reduction in viability and a reduction in WNT signaling upon induced knockdown of CSNK1ε expression. Administration of IC261 also reduced xenograft tumor cell viability in vivo and mouse survival times. An investigation of cell cycle checkpoints indicated that a majority of ovarian cancer cells with amplified c-MYC expression arrested at the G2 checkpoint of the cell cycle, but proceeded to replicate as they accumulated a greater than (>) G2 DNA content.

Inhibitors of CSNK1ε

In accordance with the foregoing, one aspect of the invention provides methods of screening for inhibitors of CSNK1ε and methods of using CSNK1ε inhibitors for inhibiting the growth and/or proliferation of a tumor comprising Myc-driven tumor cells comprising contacting the tumor cell with a CSNK1ε inhibitor. CSNK1ε inhibitors can reduce CSNK1ε kinase activity through a variety of mechanisms that are either direct or indirect. Accordingly, CSKNK1ε inhibitors can inhibit CSNK1ε at the DNA, mRNA, and polypeptide levels, targeting transcription, translation, and functional enzyme (kinase) activity.

In one embodiment, the inhibitor reduces the expression of CSNK1ε, thus reducing the levels of polypeptide product, i.e., the CSNK1ε kinase. For example, inhibition of expression can be performed by an agent that physically binds to the DNA encoding CSNK1ε, thus preventing access to the gene for transcription of the full length mRNA. Inhibition of transcription can also be accomplished, for example, by modification of the chromatin structure corresponding to the CSNK1ε gene locus.

In another embodiment, the inhibitory agent binds to or modifies the CSNK1ε mRNA molecules to prevent translation into the CSNK1ε kinase polypeptide. This can be accomplished, for example, using RNA interference. As described in Examples 1-4 below, inducible shRNA and siRNA were successfully employed to inhibit CSNK1ε expression.

In another embodiment, the CSNK1ε inhibitory agent inhibits CSNK1ε enzyme activity by binding to the CSNK1ε kinase domain or interfering with ability to bind or phosphorylate its substrate. Illustrative, non-limiting examples of such CSNK1ε inhibitory agents include small molecules, such as IC261, PF-4800567, and PF-670462. The structures of these inhibitors are illustrated below.

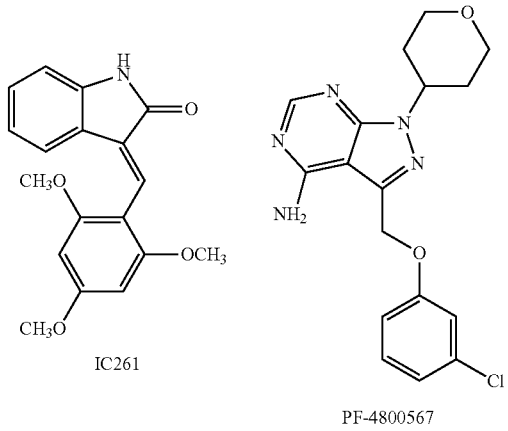

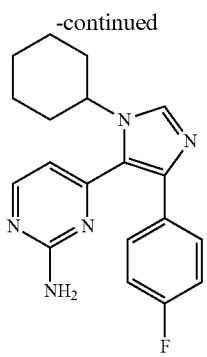

PF-670462

The CSNK1ε inhibitors identified by the method of the invention, as well as CSNK1ε inhibitors known in the art including IC261, PF-4800567, and PF-670462, can be used as therapeutic agents in the treatment of Myc-driven cancers in vivo and in vitro in accordance with the methods described herein.

In another aspect, the invention provides a method of screening for inhibitors of CSNK1ε. The method comprises contacting a Myc-driven tumor, cancer cell, or transformed cell, with a candidate CSNK1ε inhibitor agent. The Myc-driven cell is monitored for a reduction in CSNK1ε kinase activity or expression, wherein a resulting reduction in kinase activity or expression indicates that the candidate agent is an inhibitor of CSNK1ε.

In a preferred embodiment, the reduction in CSNK1ε kinase activity is determined by comparing the activity to a reference standard. In a further embodiment, the reference standard is a similar Myc-driven tumor, cancer, or transformed cell that is not contacted with the inhibitor agent. In another embodiment, the reference standard is the same Myc-driven tumor, cancer, or transformed cell before it is contacted with the inhibitor agent.

As described above, a person of skill in the art will understand that a reduction in CSNK1ε kinase activity or expression can be ascertained at the DNA, mRNA, and protein levels. Accordingly, in one embodiment, the reduction in CSNK1ε expression can be determined based on monitoring the transcriptional activity of the reduction in CSNK1ε, i.e., the relative abundance of RNA gene product. For example, commonly known methods can by applied to measure abundance of mRNA gene product, such as PCR, quantitative RT PCR. Another method is a nuclease protection assay, wherein an antisense probe (labeled with, e.g., radiolabeled or nonisotopic) hybridizes in solution to an RNA sample. Following hybridization, single-stranded, unhybridized probe and RNA are degraded by nucleases and intensity of antisense probe is determined for double stranded molecules. In yet another embodiment, Northern blot assays are used to detect and ascertain the relative amounts of RNA, such as mRNA, in a sample according to conventional Northern hybridization techniques known in the art.

In additional embodiments, RNA need not be extracted from the transformed cell or control cell. For example, fluorescent in situ hybridization can be used to determine the presence, relative quantity, and spatial distribution of target mRNA in a cell. In an illustrative example, Single Molecule RNA FISH (Biosearch Technologies, Novato, Calif.) uses multiple short singly labeled oligonucleotide probes complementary to distinct portions of the target sequence.

When each probe binds to the single stranded mRNA template, it causes cooperative unwinding of the mRNA, promoting the binding of the additional probes. The net result is the binding of a large multitude of fluorescent labels to a single molecule of mRNA template, providing sufficient fluorescence to reliably locate each target mRNA in a wide-field fluorescent microscopy image.

Detectable probes, RNA interference molecules and the like useful for any of the methods described herein may be constructed according to well-known techniques based on the human cDNA sequence of the CSNK1ε gene (Genbank Ref No. CR456429.1), set forth as SEQ ID NO:1, or naturally occurring variants thereof.

In another embodiment, the reduction in CSNK1ε kinase activity can be determined based on monitoring the amount of the polypeptide CSNK1ε kinase in the sample. For example, immunoassays such as Western blot involve immunoprecipitation of protein from a sample according to methods well-known in the art. This is followed by sodium dodecyl sulfate polyacrylamide gel electrophoresis (SDS-PAGE) of the protein sample. After separation of the proteins, immunocytochemistry and the like can by used to determine the amount of the CSNK1ε kinase present in the sample. A preferred agent for detecting a protein of interest is detectable antibody, or fragment thereof, capable of binding to the CSNK1ε kinase.

Antibodies can be generated utilizing standard techniques well known to those of skill in the art. Such antibodies can be polyclonal, or more preferably, monoclonal. An intact antibody, or an antibody fragment (e.g., Fab or F(ab')$_2$), can be used. Detectable probes, such as antibodies and the like, useful for any of the methods described herein may be constructed according to well-known techniques utilizing polypeptide moieties containing aspects of the polypeptide sequence of the CSNK1ε kinase (Genbank Ref. No. CAG30315.1) (SEQ ID NO:2), or naturally occurring variants or derivatives thereof.

Additionally, antibodies, or fragments thereof can be employed histologically, as in immunofluorescence or immunoelectron microscopy, for in situ detection of CSNK1ε protein. In situ detection can be accomplished by obtaining a histological specimen (e.g., a biopsy specimen or immobilized cell culture) and applying thereto a labeled antibody that is directed to the CSNK1ε polypeptide. The antibody (or fragment) is preferably applied onto a biological sample. Through the use of such a procedure, it is possible to determine not only the presence of the protein of interest, but also its distribution within the sample. A wide variety of well-known histological methods (such as staining procedures) can be utilized in order to achieve such in situ detection.

Antibodies can be detected via direct labeling of the antibody via, e.g., coupling (i.e., physically linking) a detectable substance to the antibody, or indirect labeling of the antibody by reactivity with another reagent that is directly labeled. Examples of indirect labeling include detection of a primary antibody using a fluorescently labeled secondary antibody. In some embodiments, the biological sample can be brought in contact with and immobilized onto a solid phase support or carrier such as nitrocellulose, or other solid support which is capable of immobilizing cells, cell particles or soluble proteins.

The support can then be washed with suitable buffers followed by treatment with the detectably labeled fingerprint gene-specific antibody. The solid phase support can then be washed with the buffer a second time to remove unbound antibody. The amount of bound label on solid support can then be detected by conventional means. A wide variety of known signaling mechanisms are also available for the described immunoassays, such as fluorescein isothiocyanate, rhodamine, phycoerythrin, phycocyanin, allophycocyanin, o-phthaldehyde fluorescamine, and the like.

In another embodiment, the reduction in CSNK1ε kinase activity can be determined based on monitoring the enzymatic activity levels of the CSNK1ε kinase in a standard kinase assay. For example, small molecules such as IC261 may be screened in a kinase assay according to the methods described in Mashhoon M., et al., "Crystal Structure of a Conformation-selective Casein Kinase-1 Inhibitor," *The Journal of Biological Chemistry* 275(26):20052-20060 (2000), hereby expressly incorporated by reference in its entirety. Briefly, standard activity assays for CSNK1ε kinase activity can be run at 37° C. The standard reaction (40 μl) contained 25 mM2-(N-morpholino)ethanesulfonic acid, pH 6.5, 50 mM NaCl, 15 mM MgCl$_2$, 2 mg/ml casein, 2 mM EGTA, 100 μM[γ-32P]ATP (100-400 cpm/pmol). Kinetic constants and their standard errors are calculated. For assay of inhibitor potency (IC$_{50}$), [γ-32P]ATP was held constant (10 μM), whereas of candidate inhibitor can be concentration was varied (such as 0.1, 0.3, 1, 3, and 10 μM). Assays contain 10 μM [γ-32P]ATP and variable concentrations of the candidate inhibitors. IC$_{50}$ values are calculated by known methods, for example, nonlinear regression algorithm of GRAPHPAD PRISM (GraphPad Software Inc.). Suitable synthetic or natural substrates containing a target amino acid sequence for measuring CSNK1ε kinase activity may also be utilized in a kinase assay.

Candidate compounds useful in the screening method include compounds from chemical libraries. Representative useful chemical libraries include libraries of structurally diverse compounds, libraries of therapeutic drug-like compounds, and libraries of therapeutic drugs approved by the Food and Drug Administration (FDA).

Myc-Driven Cancers

The normal Myc gene encodes a MYC transcription factor that has a role in the regulation of approximately 15% of all human genes. In addition to its role as a classical transcription factor, MYC is able to modify global chromatin structure by regulating histone acetylation. As described above, Myc-driven tumor cell(s) refers to a tumor cell(s) which has a genetic alteration which causes overexpression of a Myc oncogene. Such overexpression can be the result of a genetic alteration which causes deregulated mRNA expression of Myc, resulting in increased transcription rates. Moreover, overexpression can be the result of a translocation event in which the gene is adjacent to the Ig gene enhancer and therefore constitutively expressed in cells of B cell lineage, or there is a gene duplication, or amplification of the gene copy number (such as in neuroblastoma where hundreds of copies of MYCN gene are present). In such instances, the additional gene copies contribute to an increased expression signal, although any one gene locus might be regulated at a rate that would be considered normal. Nonlimiting examples of cancers exhibiting deregulated, thus over-expression of Myc are listed in Table 1.

TABLE 1

Illustrative human cancers with Myc Overexpression.

| Cancer type | Comment on Myc isotype and observed frequency of Myc deregulation |
|---|---|
| Neuroblastomas | MYCN amplification in 30% |
| Ovarian Cancer | c-Myc amplification in 30-50% and overexpression in 60-70% |

TABLE 1-continued

Illustrative human cancers with Myc Overexpression.

| Cancer type | Comment on Myc isotype and observed frequency of Myc deregulation |
|---|---|
| Rhabdomyosarcoma | MYCN amplification in 40-70% of alveolar type Rhabdomyosarcoma |
| Liver Cancer | c-Myc amplification in 30-50% and overexpression in 50-100% |
| Melanoma | c-Myc overexpression in 40-90% |
| Breast Cancer | c-Myc amplification in 20-50% of total, 90% in ductal type |
| Colon Cancer | c-Myc overexpression in 70% |
| Prostate Cancer | c-Myc amplification in 30-60% |
| Burkitt's lymphomas | c-Myc translocation occur in all subtypes |
| Lung Cancer | c-Myc, L-Myc and MYCN |

In one embodiment of the method, the Myc-driven tumor cell is of neural origin. Cancers having neural origins include tumor cells derived from a primary neuroblastoma tumor, a metastatic neuroblastoma tumor or a brain tumor, which is caused by cancer of brain cells, metastatic brain cancer, which is cancer of another part of the body that has spread to the brain. Further examples of cancers of neural origin include, but not limited to: neuroblastoma; glioma (astrocytoma, glioblastoma, oligodendroglioma, schwannoma); medulloblastoma, also known as primitive neuroectodermal tumors (PNET); acoustic neuroma; pineocytoma and pineoblastoma; retinoblastoma; meningioma; ependymoma; brain stem gliomas; craniopharyngiomas; pineal region tumors neurocytomas; and ganglioneuromas.

A review of the body atlas of CSNK1ε expression demonstrated that the tissues with the highest expression are brain/fetal and pineal body. Additionally, among the 28 tissues of highest CSNK1ε expression, 15 are of neural origin, including brain/cerebellum, corpus callosum, thalamus, subthalamic nucleus, pons, amygdaloid body, hypothalamus, frontal lobe, prefrontal cortex, dorsal root ganglia, and caudate nucleus. Additionally, reference to the Oncogenomics Database indicated that CSNK1ε is highly expressed in clinical samples of neuroblastoma cells that exhibit aberrant or high levels of n-MYC expression.

In another embodiment, the Myc-driven cancer is an ovarian cancer. In another embodiment, the Myc-driven cancer is selected from the group consisting of rhabdomyosarcoma, liver cancer, melanoma, breast cancer, colon cancer, prostate cancer, Burkitt's lymphoma and lung cancer.

In one aspect, the present invention provides methods for inhibiting the growth and/or proliferation of Myc-driven tumor cells comprising contacting the cells with a CSNK1ε inhibitor. In one embodiment, the tumor cell is contacted in vitro. In another embodiment, the tumor cell is contacted in vivo in a mammalian subject. In some embodiments, the mammalian subject is a primate, rodent, canine, feline, horse or cow.

In preferred embodiments, the mammalian subject is a human. In one embodiment, the CSNK1ε inhibitor is a small molecule. In some embodiments small molecule inhibitor of CSNK1ε is at least one of IC261, PF-4800567 or PF-670462.

In another aspect, the invention provides a method of treating a subject suffering from a tumor comprising myc-driven tumor cells, comprising administering to the subject an amount of a composition comprising a CSNK1ε inhibitor effective to inhibit the growth and/or proliferation of the tumor cells. Examples of Myc-driven cancers are described herein. In some embodiments, the subject is suffering from a myc-driven cancer of neural origin, examples of which are provided herein. In some embodiments, the myc-driven tumor cell of neural origin is derived from a primary neuroblastoma tumor, a metastatic neuroblastoma tumor or a brain tumor. In some embodiments, the subject is suffering from an ovarian cancer comprising myc-driven tumor cells. In some embodiments, the subject is suffering from a cancer comprising myc-driven tumor cells selected from the group consisting of rhabdomyosarcoma, liver cancer, melanoma, breast cancer, colon cancer, prostate cancer, Burkitt's lymphoma and lung cancer.

In some embodiments, the method further comprises the step of determining whether the tumor in said subject comprises myc-driven tumor cells prior to treatment with said composition comprising a CSNK1ε inhibitor. The step of determining whether the tumor in said subject comprises myc-driven tumor cells may be carried out by accessing a database, or by assaying cells obtaining from the subject (such as a biopsy sample from said subject) for an aberrantly high level of Myc protein or mRNA expression as compared to normal cells (or as compared to a reference standard), or by assaying cells obtained from the subject for the presence of amplified gene copies of cDNA encoding Myc, using standard methods known in the art and as further described herein.

In some embodiments, the composition comprising a CSNK1ε inhibitor is effective to selectively inhibit the growth and/or proliferation of the myc-driven tumor cells, while not inhibiting the growth and proliferation of non-myc driven cells (i.e. cells with normal, low levels of myc).

Administration of the composition comprising a CSNK1ε inhibitor effective to inhibit the growth and/or proliferation of the myc-driven tumor cells can be performed according to a variety of well-known methods, which can include steps for inhibiting tumor cells including providing the inhibitor in a pharmaceutical carrier, methods of administration to a cell in vitro (in cell culture), or administration to a mammalian subject in vivo by any mode known in the art which retains agent activity and provides access to the cancer cells. These include, without limitation, oral, intravenous, intraperitoneal, subcutaneous, intramuscular, and intrathecal routes of administration.

Pharmaceutical compositions comprising CSNK1ε inhibitors are also provided. Such a composition contains from about 0.01 to 90% by weight (such as 1 to 20% or 1 to 10%) of the CSNK1ε inhibitor in a pharmaceutically acceptable carrier. Solid formulations of the compositions for oral administration may contain suitable carriers or excipients, such as corn starch, gelatin, lactose, acacia, sucrose, microcrystalline cellulose, kaolin, mannitol, dicalcium phosphate, calcium carbonate, sodium chloride, or alginic acid. Liquid formulations of the compositions for oral administration prepared in water or other aqueous vehicles may contain various suspending agents such as methylcellulose, alginate, tragacanth, pectin, kelgin, carageenan, acacia, polyvinylpyrrolidone, and polyvinyl alcohol.

Injectable formulations of the compositions comprising a CSNK1ε inhibitor may contain various carriers such as vegetable oils, dimethylacetamide, dimethylformamide, ethyl lactate, ethyl carbonate, isopropyl myristate, ethanol, or polyols (glycerol, propylene glycol, liquid polyethylene glycol and the like). For intravenous injections, water soluble versions of the compounds may be administered by the drip method, whereby a pharmaceutical formulation containing an antifungal agent and a physiologically acceptable excipient is infused. Physiologically acceptable excipients may include, for example, 5% dextrose, 0.9% saline, Ringer's solution, or other suitable excipients. Intramuscular preparations, e.g., a sterile formulation of the compounds of the invention, can be dissolved and administered in a pharmaceutical excipient such as water-for-injection, 0.9% saline, or 5% glucose solution.

Conventional methods, known to those of ordinary skill in the art of medicine, can be used to administer the pharmaceutical formulations to a mammalian subject. The pharmaceutical formulations can be administered via oral, subcutaneous, intrapulmonary, transmucosal, intraperitoneal, intrauterine, sublingual, intrathecal, intramuscular, nasal, rectal, vaginal, and other routes of delivery that effectively result in dispersion of the delivered agent to a single or multiple sites of intended therapeutic action.

The compositions comprising a CSNK1ε inhibitor in accordance with the invention may be systemically or locally administered on a periodic basis at intervals determined to maintain a desired level of therapeutic effect. For example, a composition comprising a CSNK1ε inhibitor may be administered, such as by subcutaneous injection, daily, weekly, every two to four weeks or at greater or less frequent intervals. The dosage regimen will be determined by the physician considering various factors that may influence the action of the combination of agents. These factors will include the extent of progress of the condition being treated, the patient's age, sex and weight, and other clinical factors. The dosage for each individual agent will vary as a function of the inhibitory agent that is included in the composition, as well as the presence and nature of any drug delivery vehicle (e.g., a sustained release delivery vehicle).

In some embodiments of the method, the subject suffering from a tumor comprising myc-driven tumor cells is further provided with one or more additional anti-cancer therapies. The additional therapies can include surgery, chemotherapy using chemical therapeutic agents distinct from the CSNK1ε inhibitor, and radiation therapy. In some embodiments, the additional therapies include administration of an inhibitor of SHH expression or activity and/or an inhibitor of WNT expression or activity.

In one embodiment, the myc-driven tumor cell exhibits resistance, or some level of reduced sensitivity to the additional chemotherapeutic agent, and the administration of the additional chemotherapeutic agent with the CSNK1ε inhibitor renders the tumor cells susceptible to the additional chemotherapeutic agent. In one embodiment, the myc-driven tumor comprises cells that are resistant to cisplatin and the CSNK1ε inhibitor renders the cells susceptible to cisplatin. Accordingly, in some embodiments, the composition containing the CSNK1ε inhibitor is administered to a subject undergoing treatment with cisplatin. In one embodiment, the invention provides a composition comprising a CSNK1ε inhibitor in combination with a chemotherapeutic agent, such as Cisplatin.

In another aspect, the invention provides a method for identifying compounds capable of inhibiting proliferation of a myc-driven cancer cell. The method comprises contacting a myc-driven cancer cell line expressing CSNK1ε with a candidate compound in cell culture. Then a determination is made of at least one of: (i) the level of WNT expression or activity in the presence and absence of the candidate compound, (ii) the level of SHH expression or activity in the presence and absence of the candidate compound, or (iii) the level of CSNK1ε expression or activity in the presence and absence of the candidate compound. A decrease in the expression level or activity of WNT; and/or a decrease in the expression level or activity of SHH, and/or a decrease in the expression level or activity of CSNK1ε in the presence of the candidate compound is indicative of a compound that inhibits proliferation of a cancer cell.

Detection of WNT, SHH or CSNK1ε expression or activity can be performed by methods well known in the art. For example, methods for detection of mRNA and polypeptide gene products to indicate expression levels are described above. Additionally, detection of signaling activity can be performed using well-known reporter assays. For example, as described in Example 3 and 4, a WNT dual reporter system employing consensus (TOP) and mutant (FOP) TCF binding sites to assay the β-catenin activity. β-catenin activity is a functional reporter of WNT signaling, and therefore, its detection according to this methods permits the measurement of WNT signaling in response to experimental systems. Additionally, a similar dual reporter SHH system is described in Example 3 utilizing Gli detectable reporters to permit the assaying of SHH signaling. Accordingly, in further embodiments, the method comprises a tumor cell line comprising a gene operationally linked to WNT. In another embodiment, the method comprises a tumor cell line comprising a gene operationally linked to SHH.

In some embodiments, the myc-driven cancer cell line expressing CSNK1ε is a neuroblastoma cell or an ovarian cancer cell. In some embodiments, the cancer cell line comprises a reporter gene operationally linked to WNT. In some embodiments, the candidate compound is from a library of structurally diverse compounds, a library of therapeutic drug-like compounds, or a library of therapeutic drugs approved by the Food and Drug Administration (FDA).

The following examples merely illustrate the best mode now contemplated for practicing the invention, but should not be construed to limit the invention. All literature citations are expressly incorporated by reference.

Example 1

This Examples describes the use of inhibitors of CSKN1ε to inhibit proliferation of neuroblastoma cells in vitro.

Rationale

In an siRNA screen in human fibroblast derived cells, it was determined that short hairpin RNAs (shRNAs) targeting CSNK1ε induced growth inhibition in these engineered cells (Yang, W. S., and B. R. Stockwell, "Inhibition of Casein Kinase 1-epsilon Induces Cancer-Cell-Selective, PERIOD2-Dependent Growth Arrest," *Genome Biology* 9:R92, 2008). An examination of the CSNK1ε gene sequence revealed several putative MYC-MAX binding sites in the promoter regions around Exon 1. Neuroblastoma is a pediatric cancer that often presents with amplification MYCN, the neuronal expressed homologue of c-MYC, for review see Park, J., et al., "Neuroblastoma: Biology, Prognosis and Treatment," *Pediatric Clinics of North America* 55:97-120, 2008. MYCN is a well-documented driver of neuroblastoma initiation and maintenance in mouse models (Weiss, W. A., et al., "Targeted Expression of MYCN Causes Neuroblastoma in Transgenic Mice," *Embo J* 16:2985-2995, 1997) and the strongest molecular marker of poor prognosis (Riley, R. D., et al., "A Systematic Review of Molecular and Biological Tumor Markers in Neuroblastoma," *Clin Cancer Res* 10:4-12, 2004). This hypothesis stems from the shared c-MYC and MYCN transcriptional programs and cellular phenotypes (Boon, K., et al., "N-myc Enhances the Expression of a Large Set of Genes Functioning in Ribosome Biogenesis and Protein Synthesis," *EMBO J* 20:1383-1393, 2001; Mestdagh, P., et al., "MYCN/c-MYC-Induced microRNAs Repress Coding Gene Networks Associated With Poor Outcome in MYCN/c-MYC-Activated Tumors," *Oncogene* 29:1394-1404) and by the observation that c-MYC can functionally replace MYCN during murine development (Malynn, B. A., et al., "N-myc Can Functionally Replace c-myc in Murine Development, Cellular Growth, and Differentiation," *Genes Dev* 14:1390-1399, 2000). Additionally, reference to microarray data available at Oncogenomics neuroblastoma prognosis database indicated that survival of neuroblastoma segregated on the basis of CSNK1ε expression. Specifically, neuroblastoma patients with high CSNK1ε had significantly shorter survival than patients with low CSNK1ε.

Therefore, the inventors investigated CSNK1ε as a novel therapeutic target for cancers of neural origin, specifically in neuroblastoma cells, as described below.

Methods and Results

CSNK1ε Expression is Elevated in Neuroblastoma Cells with High MYCN Expression.

An examination of the CSNK1ε gene sequence revealed several putative MYC-MAX binding sites in the promoter regions around Exon 1. This observation indicated that CSNK1ε is a potential transcriptional target of MYC. This hypothesis was further supported by the observation that CSNK1ε was induced in a transgenic neuroblastoma cell line containing a tetracycline-inducible vector encoding MYCN (data not shown).

In order to determine whether a correlation exists between high MYCN levels and CSNK1ε expression, CSNK1ε and MYCN protein levels were assayed by Western Blot from three different neuroblastoma cell lines: SK-N-AS, SK-N-BE2 and IMR-32. Protein was extracted from cell lysates of SK-N-AS, SK-N-BE2 and IMR-32 neuroblastoma cell lines using standard protein isolation techniques known in the art. The extraction samples were separated by SDS-PAGE electrophoresis and blotted according to standard protocols with the following antibodies: anti-CSNK1ε (610445, BD Biosciences), anti-n-Myc (NCM-II, Santa Cruz Biotechnology), and anti-Actin (AC-15, abcam, Cambridge, UK). Quantitation of the Western blot was performed using ImageJ software (NIH).

As illustrated in FIG. 1A, dense bands indicating high levels of CSNK1ε protein product were detected in neuroblastoma cells lines SK-N-BE2 and IMR-32, which also displayed overexpression of MYCN. In contrast, SK-N-AS neuroblastoma cells had minimal CSNK1ε protein product and no detectable MYCN protein product. An expanded Western Blot analysis incorporating five additional neuroblastoma cell lines (SH-SY-5Y, NBL-W-N, KCN, KCNR, and LA-N-5) was also conducted. Polypeptide levels were detected using antibodies specific for MYCN, MYC (polyclonal), CSNK1ε, and Actin. Comparison of CSNK1ε/Actin expression to MYCN/Actin expression revealed a positive correlation ($R2=0.639$; $p-0.038$) between CSNK1ε and MYCN expression in the neuroblastoma cells.

Figure 1B:
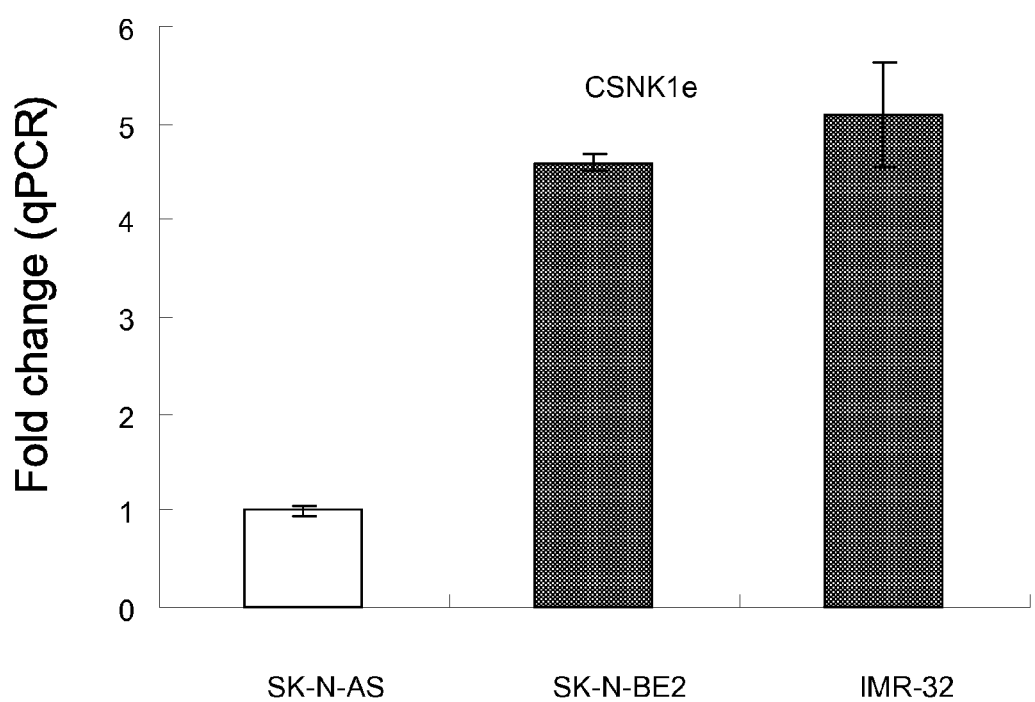
FIG. 1B is a bar graph illustrating the gene expression levels of CSNK1ε in neuroblastoma cells with or without amplified MYCN expression; as described in Example 1.

The positive correlation between CSNK1ε and MYCN expression was also confirmed at the transcriptional level. RNA was extracted from cultures of SK-N-AS, SK-N-BE2 and IMR-32 neuroblastoma cell lines according to standard protocols. mRNA corresponding to CSNK1ε was reverse transcribed and amplified using quantitative RT PCR using standard cycling parameters. As illustrated in FIG. 1B, between 4 and 5-fold more CSNK1ε mRNA was detected by qRTPCR in the neuroblastoma cell lines, SK-N-BE2 and IMR-32, known to over-express n-MYC, as compared to a control neuroblastoma line, SK-N-AS, which does not over express n-MYC.

Figure 2:
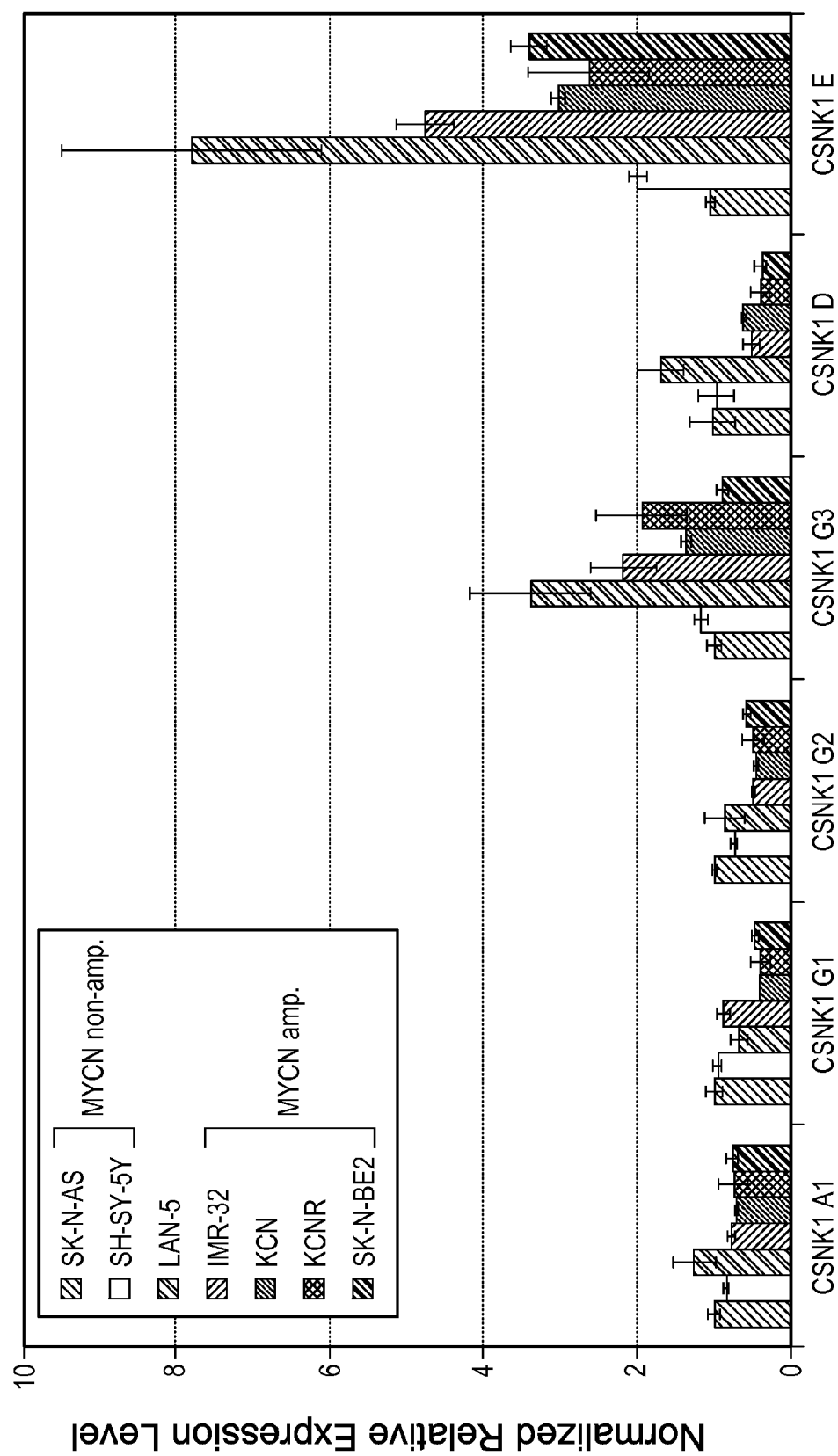
FIG. 2 is a bar graph illustrating relative expression of CSNK isoforms in neuroblastoma cells with or without amplified MYCN expression, as determined by qRT-PCR; as described in Example 1.

There are six different isoforms of CSNK1, which are encoded by separate genes (Hanks, S. K., and T. Hunter, T., "Protein Kinases 6: The Eukaryotic Protein Kinase Superfamily: Kinase (Catalytic) Domain Structure and Classification," *Faseb J* 9:576-596, 1995). In order to analyze the role of Myc in the regulation of the CSNK1ε gene, MYCN expression and CSNK1ε expression was investigated for all CSNK1 isotypes to determine if there was a correlation. Neuroblastoma cells with different MYCN expression levels were analyzed by qRT-PCR to determine the expression pattern of different CSNK1 isoforms and any correlation with amplified MYCN expression. Seven neuroblastoma cell lines were used. The neuroblastoma lines SK-N-AS and SH-SY-5Y have low, or non-amplified MYCN expression, whereas the neuroblastoma lines LAN-5, IMR-32, KCN, KCNR, and SK-N-BE2 have amplified MYCN expression. As illustrated in FIG. 2, the epsilon isoform was the predominant isoform of CSNK1 expressed in neuroblastoma cell lines that also had amplified MYCN expression. Therefore, the correlation and functional relationship between MYCN and CSNK1ε expression appeared to be specific for the epsilon isoform of CSNK1.

Taken together, these data indicate that CSNK1ε expression correlates with the high expression of the MYCN oncogene in multiple, high MYCN expressing neuroblastoma cell lines. Furthermore, MYCN appears to directly regulate transcription of the CSNK1ε gene. This indicates that CSNK1ε is important for the viability of cells with amplified MYCN expression, thereby making CSNK1ε a potential therapeutic target in Myc-driven cancer cells of neural origin.

Knock-Down of CSNK1 Expression Reduced Viability of Cells with Amplified MYCN Expression.

To test the effect of CSNK1ε inhibition on the growth of neuroblastoma cell lines, lentiviral vectors were constructed that enable the conditional knock-down of CSNK1ε upon induction by doxycycline ("Dox"), a semi-synthetic tetracycline compound. SK-N-BE2 neuroblastoma cells (with MYCN gene amplification) were transfected with a control shRNA construct, and the following two shRNA constructs corresponding to two different target sequences of the CSNK1ε mRNA sequence. The two core target sequences of CSNK1e used in the dox inducible shRNA are listed below:

```
                                          (SEQ ID NO: 3)
        CSNK1e sh#1 (GGCTATCCCTCCGAATTCT)

(SEQ ID NO: 4)
        CSNK1e sh#2 (GAACGGATCAGCGAGAAGA)
```

Figure 3A:
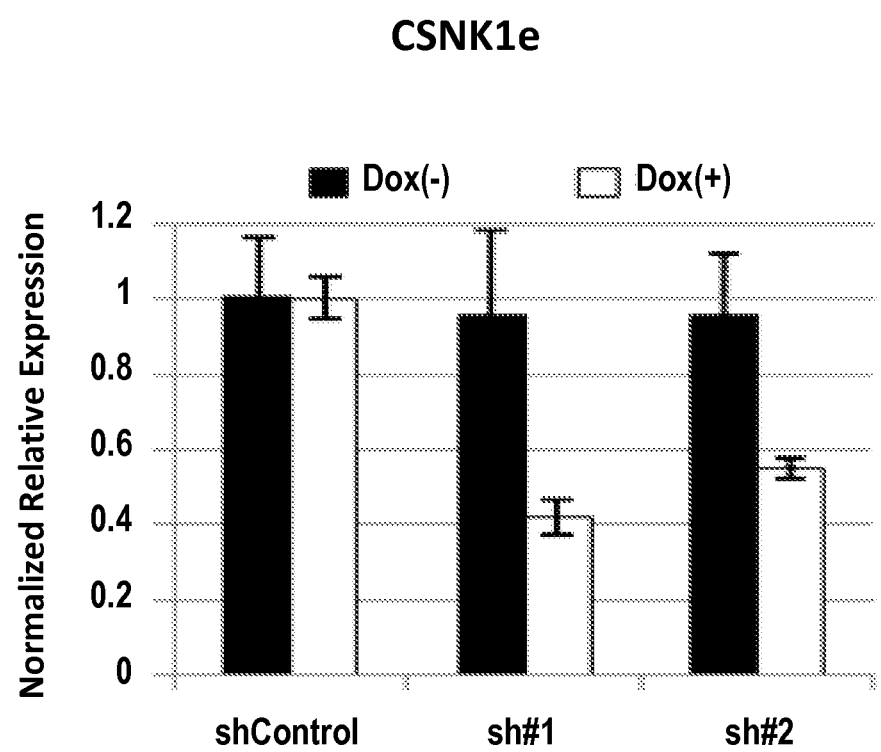
FIG. 3A is a bar graph illustrating relative levels of CSNK1ε mRNA in neuroblastoma cells with or without Dox induced siRNA silencing, as determined by qRT-PCR; as described in Example 1.
Figure 3B:
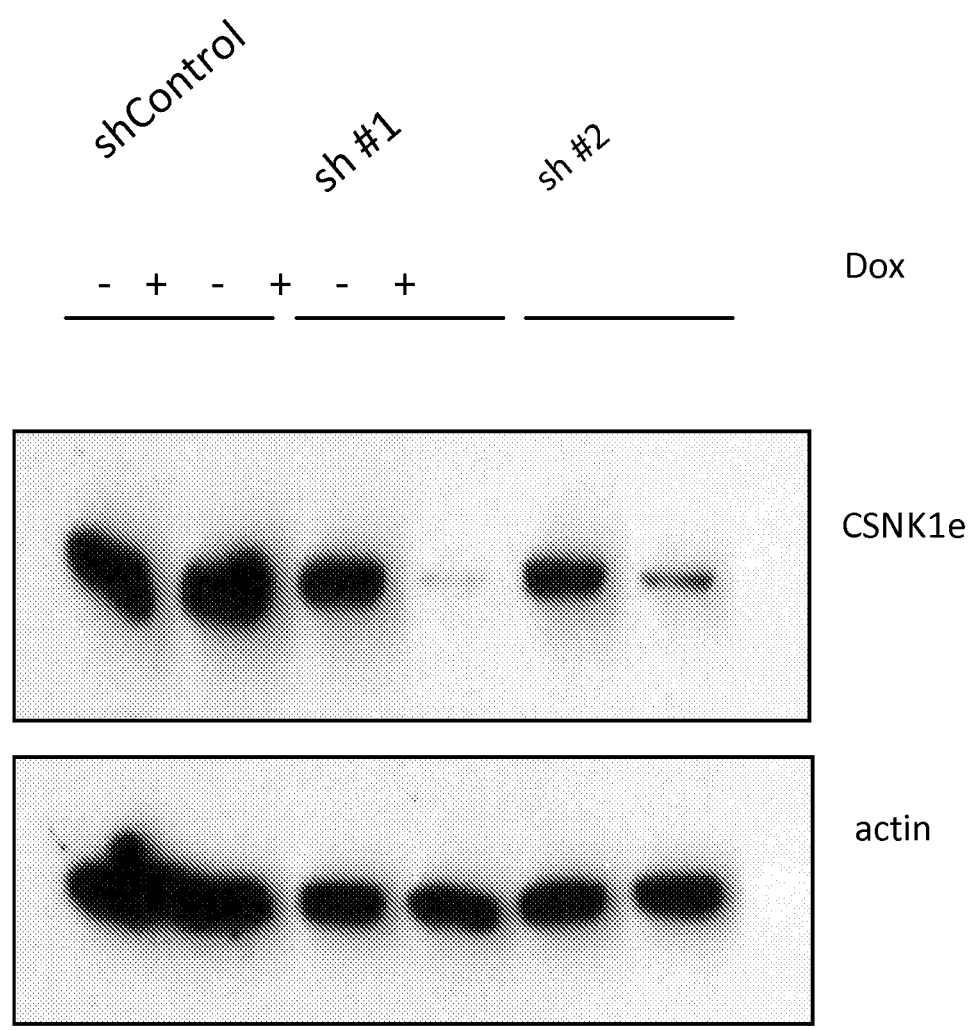
FIG. 3B is a Western blot illustrating relative levels of CSNK1ε protein in neuroblastoma cells with or without induced of siRNA silencing; as described in Example 1.

The shRNA encoding plasmids were transfected into the cells and were cultured in the presence or absence of Dox for 4 days before gene expression levels were quantified with qPCR. FIG. 3A illustrates that the relative expression of CSNK1ε fell to between about 0.4 and about 0.6 of normal levels upon Dox-induced expression of the first and second shRNA constructs corresponding to CSNK1ε, respectively. This was confirmed at the protein level by Western blot analysis where the measurable protein levels of CSNK1ε gene product were reduced in transfected cells treated with Dox. See FIG. 3B. This demonstrates the effectiveness of the inducible lentivirus vector encoding CSNK1ε siRNAs to knockdown expression of the CSNK1ε gene and the corresponding polypeptide gene product. Notably, the knockdown of CSNK1ε did not affect expression of the other isoforms, as determined by qPCR, indicating the specificity of the shRNA targeting hairpin (data not shown).

Figure 3C:
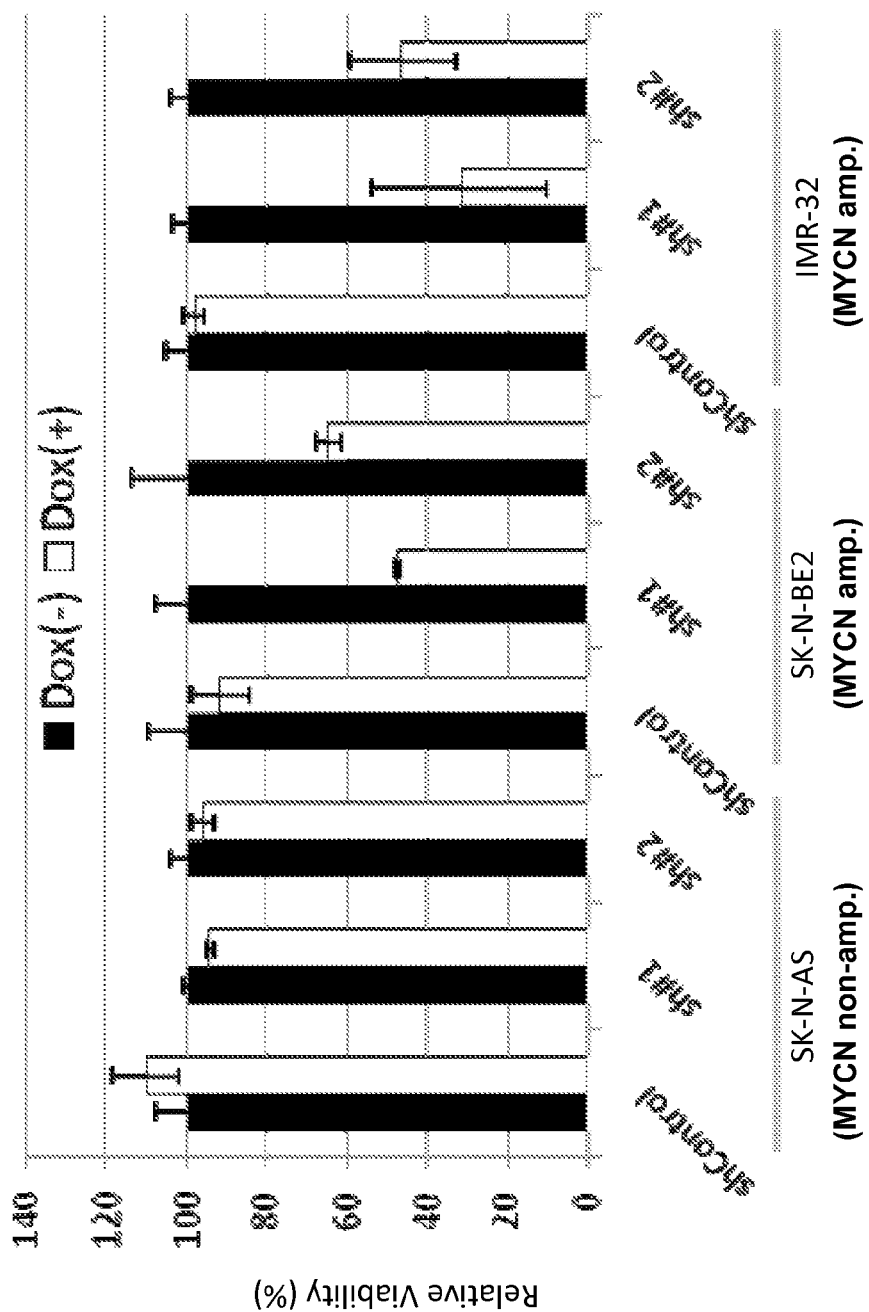
FIG. 3C is a bar graph illustrating viability of neuroblastoma cells with MYCN amplification (SK-N-BE2 and IMR-32) or without MYCN amplification (SK-N-AS) upon transduction with lentivirus constructs encoding inducible shRNAs targeted at two CSNK1ε sequences and a control sequence; as described in Example 1.

Lentiviral vectors expressing Dox-inducible shRNAs targeting CSNK1ε were transduced into SK-N-AS, a neuroblastoma line with normal MYCN expression, and SK-N-BE2 and IMR-32, neuroblastoma lines with amplified MYCN expression. Expression of the shRNAs were induced with Dox and cell viability was assayed after four days using the CellTiter Glo assay (Promega, Madison, Wis.). As illustrated in FIG. 3C, induction of both CSNK1ε shRNA constructs caused a substantial loss of cell viability in the neuroblastoma cells lines with amplified MYCN (SK-N-BE and IMR32), but not in neuroblastoma cells with normal MYCN expression (SK-N-AS). This demonstrates that expression of CSNK1ε is required only in the context of aberrant, enhanced expression of the MYC oncogene in neuroblastoma cells.

Figure 3D:
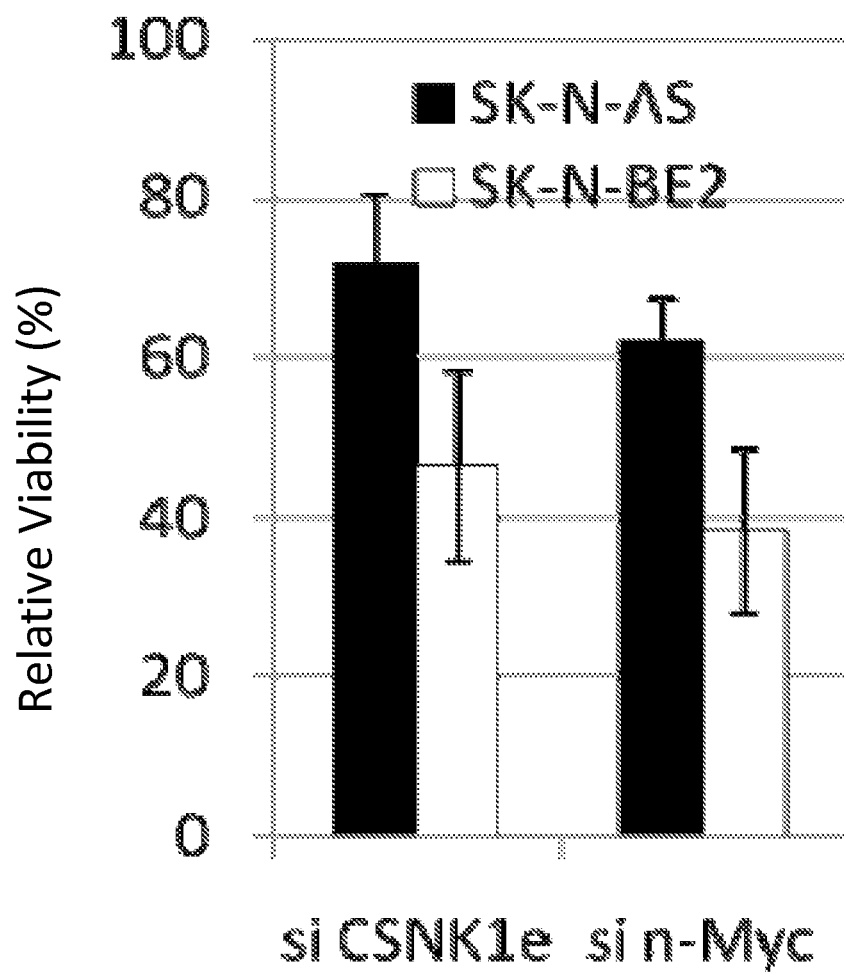
FIG. 3D is a bar graph illustrating the effects of CSNK1ε or MYCN transient knockdown with siRNAs on cell viability in neuroblastoma cells with MYCN amplification (IMR-32) and without MYCN amplification (SK-N-AS), wherein the cells were transfected with siRNA pools specific for each gene (three different duplexes), and viability was assayed 96 hours post-transfection; as described in Example 1.

Additionally, the effects of CSNK1ε or MYCN transient knock-down upon cell viability were assessed in SK-N-AS and IMR-32 cells. The cells were transfected with siRNAs pools (three different duplexes) specific for each gene. At 96 hours post-transfection, viability of the cells was measured by CellTiter-Glo assay (Promega, Madison, Wis.). As illustrated in FIG. 3D, the transient knockdown of both CSNK1ε and MYCN resulted in a significantly greater reduction in the cell viability in the neuroblastoma cells with amplified MYCN (SK-N-BE) as compared to the neuroblastoma cells with normal MYCN expression (SK-N-AS). The data shown in FIG. 3D represents the mean viability±SD relative to cells transduced with a control constructs.

Chemical Inhibition of CSNK1 Kinase Activity Blocks Growth of Neuroblastoma.

Figure 4A:
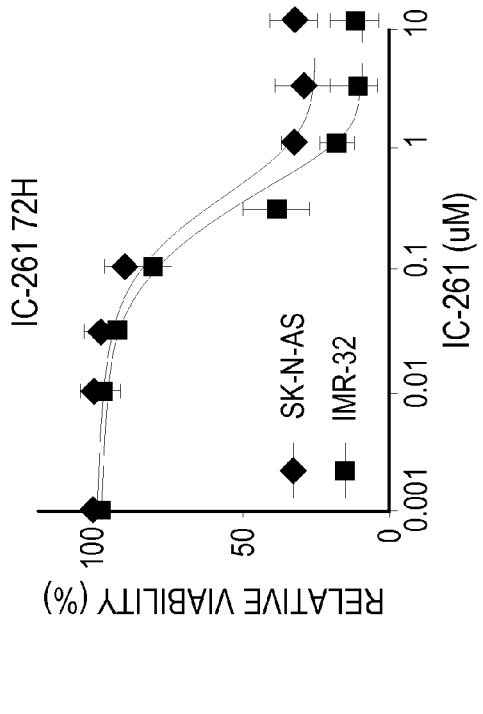
FIG. 4A is a graph illustrating the viability of neuroblastoma cells with MYCN amplification (IMR-32) and without MYCN amplification (SK-N-AS), as a function of IC261 concentration, wherein viability was assayed at 48 hours after treatment; as described in Example 1.
Figure 4B:
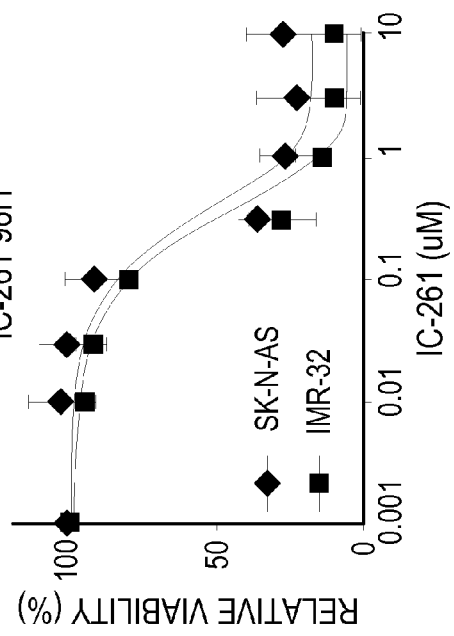
FIG. 4B is a graph illustrating the viability of neuroblastoma cells with MYCN amplification (IMR-32) and without MYCN amplification (SK-N-AS), as a function of IC261 concentration, wherein viability was assayed at 72 hours after treatment; as described in Example 1.
Figure 4C:
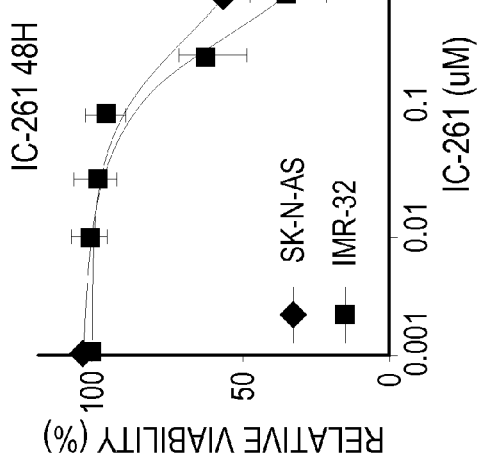
FIG. 4C is a graph illustrating the viability of neuroblastoma cells with MYCN amplification (IMR-32) and without MYCN amplification (SK-N-AS), as a function of IC261 concentration, wherein viability was assayed at 96 hours after treatment; as described in Example 1.

To evaluate the therapeutic potential of CSNK1ε kinase inhibitors for the inhibition of tumor cell growth, the kinase function of CSNK1ε polypeptide was blocked with IC261, a small molecule inhibitor of CSNK1ε and d kinase activity (Mashhoon, N., et al., "Crystal Structure of a Conformation-Selective Casein Kinase-1 Inhibitor," *J Biol Chem* 275: 20052-20060, 2000). Specifically, the sensitivity of MYC overexpressing cells to IC261 relative to control, was determined in vitro utilizing the neuroblastoma cell lines SK-N-AS (normal MYCN expression) and IMR-32 (amplified MYCN expression). Cultured cells were treated with a range of concentrations of IC261 and percent of cell viability was recorded over four days as described above. After only 48 hours with IC261 concentrations of 0.33 µg/ml and higher, IMR-32 neuroblastoma cells (amplified MYCN expression) exhibited a lower percent cell viability compared to SN-N-AS neuroblastoma cells (normal MYCN expression). The difference in cell viability was significant at the 1, and 10 µM concentrations. See FIG. 4A. The significant difference in cell viability between the neuroblastoma cell lines persisted to 72 hours. See FIG. 4B. The difference between viability of neuroblastoma cells lines persisted even to 96 hours at the higher doses (but the difference was not statistically significant). See FIG. 4C.

Figure 5:
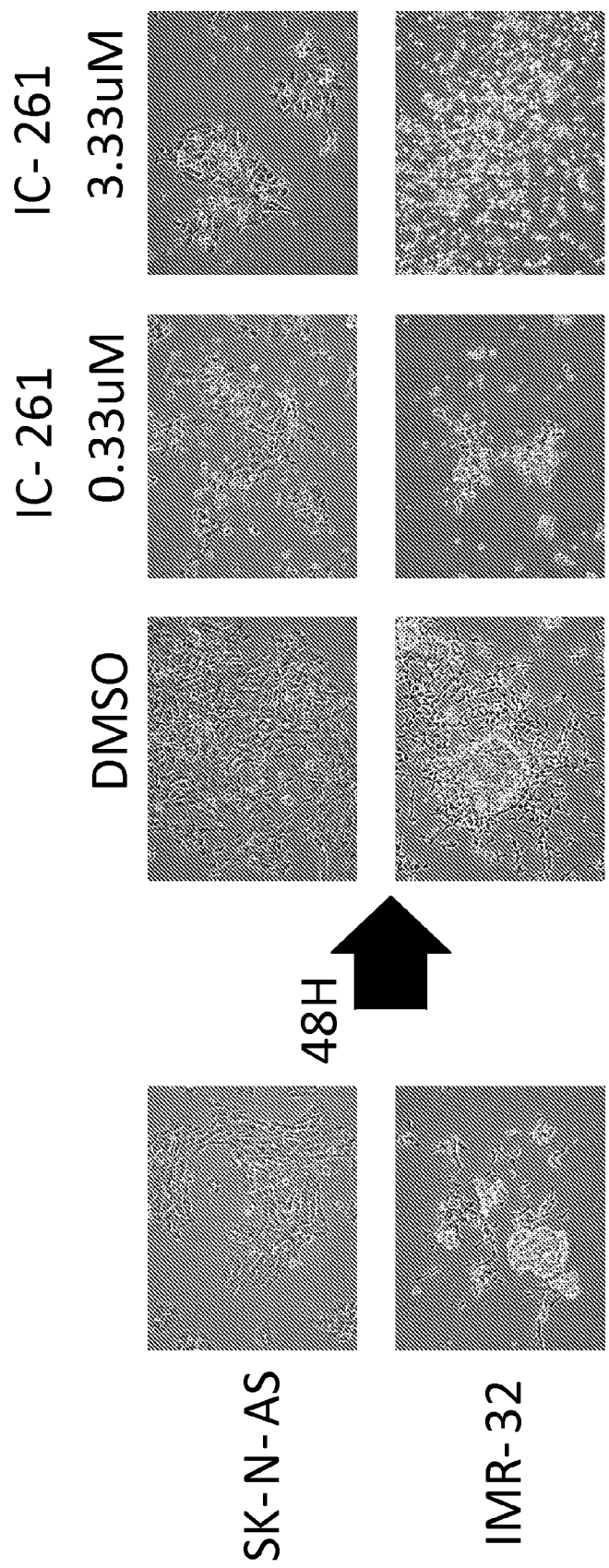
FIG. 5 shows a series of micrographs illustrating neuroblastoma cells with MYCN amplification (IMR-32) and without MYCN amplification (SK-N-AS) before and 48 hours after exposure to IC261; as described in Example 1.
Figure 6A:
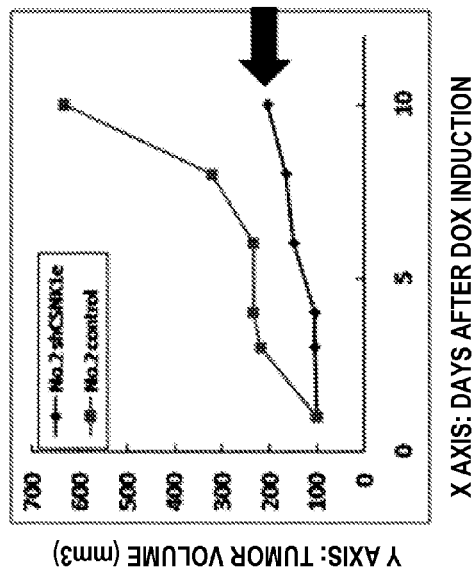
FIGS. 6A-D graphically illustrate the tumor volume in four mice with engrafted tumors, wherein the tumor cells have amplified MYC expression (SK-N-BE2) and contain lentiviral vectors encoding Dox-inducible shRNAs specific for CSNK1ε or control, wherein tumor volume is expressed over time after shRNA induction by Dox; as described in Example 2.
Figure 6B:
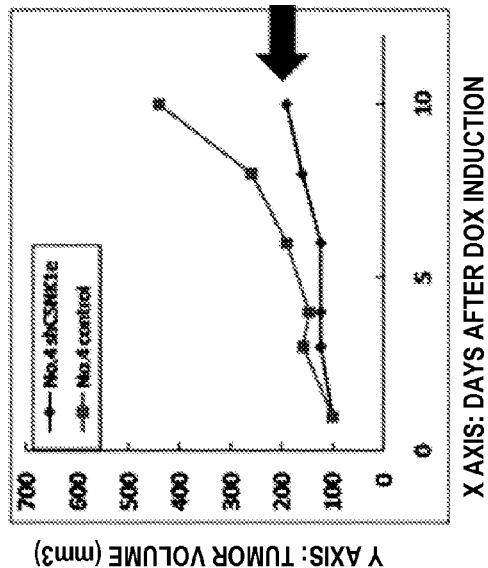
Figure 6C:
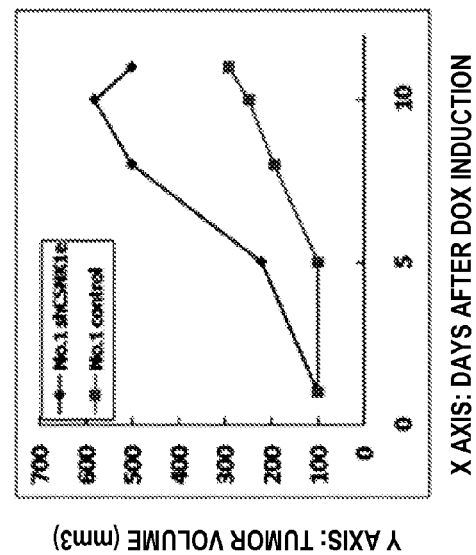
Figure 6D:
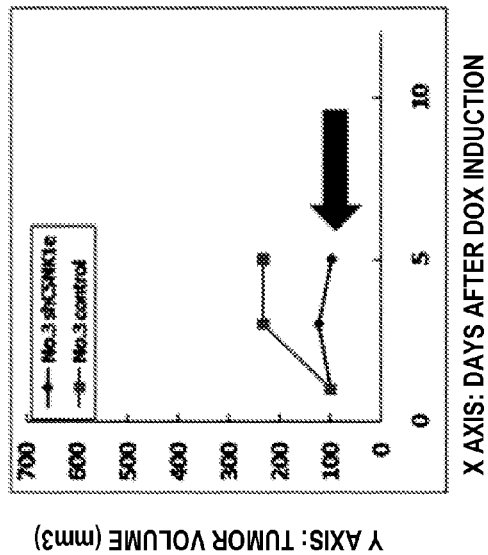

Microscopic analysis of the SN-N-AS (normal MYCN expression) and IMR-32 (amplified MYCN expression) neuroblastoma cell lines, further supporting the differential effect of the CSNK1ε inhibitor, IC261, on the health and proliferation of neuroblastoma cells overexpressing MYCN. Referring to FIG. 5, top line, micrographs are provided illustrating SK-N-AS (normal MYCN expression) cells in culture before and 48 hours after culture with DMSO, 0.33 µM, or 3.3 µM IC261. Referring to FIG. 5, bottom line, micrographs are provided illustrating IMR-32 cells (amplified MYCN expression) in culture before and 48 hours after culture with DMSO, 0.1 µM, or 1.0 µM IC261. Pre-treatment cells and DMSO-treated cells from both lines exhibited healthy spreading. However, after 48 hours of treatment of IC261, the majority of IMR-32 blastoma cells appeared to have detached from the plate surface and balled up, whereas a large proportion of the SN-N-AS maintained healthy spreading and attachment. These results demonstrate that CSNK1ε function is not required for growth and proliferation of cells with normal MYCN levels, however, CSNK1ε is required for growth and proliferation of cells with aberrantly high expression of MYCN (i.e., amplified MYCN).

Conclusion

These data demonstrate that expression of CSNK1ε is elevated in neuroblastoma cells with amplified expression of MYCN. Further, these results demonstrate that MYCN directly regulates the transcription of CSNK1ε. Moreover, these results demonstrate that knockdown of CSNK1ε expression, or chemical inhibition of the CSNK1ε kinase function specifically reduces the viability of neuroblastoma cells with amplified MYCN levels, but does not inhibit viability of cells with normal MYCN levels. Thus, CSNK1ε is only required in the context of aberrant, enhanced expression of the MYC oncogene in neuroblastoma cells. These results establish CSNK1ε as a viable therapeutic target for inhibiting growth and/or proliferation of MYC-driven tumor cells.

Example 2

This Example demonstrates the use of inhibitors of CSKN1ε to inhibit proliferation of neuroblastoma cells in vivo in a mouse xenograft model.

Rationale

As described in Example 1, CSNK1ε expression was found to be associated with elevated MYCN expression in neuroblastoma cells. Additionally, CSNK1ε expression and kinase function was found to be required for continued viability of neuroblastoma cells with aberrantly high MYCN expression. Therefore, inhibition of CSNK1ε in established tumors with high MYCN expression was investigated in vivo.

Methods and Results

Knock-Down and Chemical Inhibition of CSNK1 Kinase Activity Blocks Growth of Neuroblastoma Xenografts.

The efficacy of CSNK1ε knock-down (expression and functional knockdown) in the inhibition of tumor growth in vivo was tested in a therapeutic model of neuroblastoma xenograft mice using the SK-N-BE2 and IMR-32 cell lines, respectively.

To establish the viability of CSNK1ε as target for cancer therapeutics, expression of CSNK1ε was knocked down using inducible shRNA interference in established SK-N-BE2 (amplified MYCN expression) xenograft blastoma tumors. Specifically, SK-N-BE2 cells were transduced in vitro with Dox-inducible lentivirus vectors encoding shRNA targeting the CSNK1ε mRNA or a control, as described above in Example 1, and injected into mice as follows. Approximately $2 \times 10^6$ cells were subcutaneously injected in the flank of NOD/SCID mice. The resulting engrafted tumors were permitted to establish for 2-3 weeks. The mice were then injected daily for seven days with 1 mg/ml Dox in 5% sucrose water. As illustrated in FIGS. 6A-D, three out of four mice with tumors containing the shCSNK1ε vectors exhibited inhibition of tumor growth upon Dox induction, indicating that silencing of CSNK1ε was effective in blocking growth of neuroblastoma cells with aberrantly high MYCN expression.

Figure 7A:
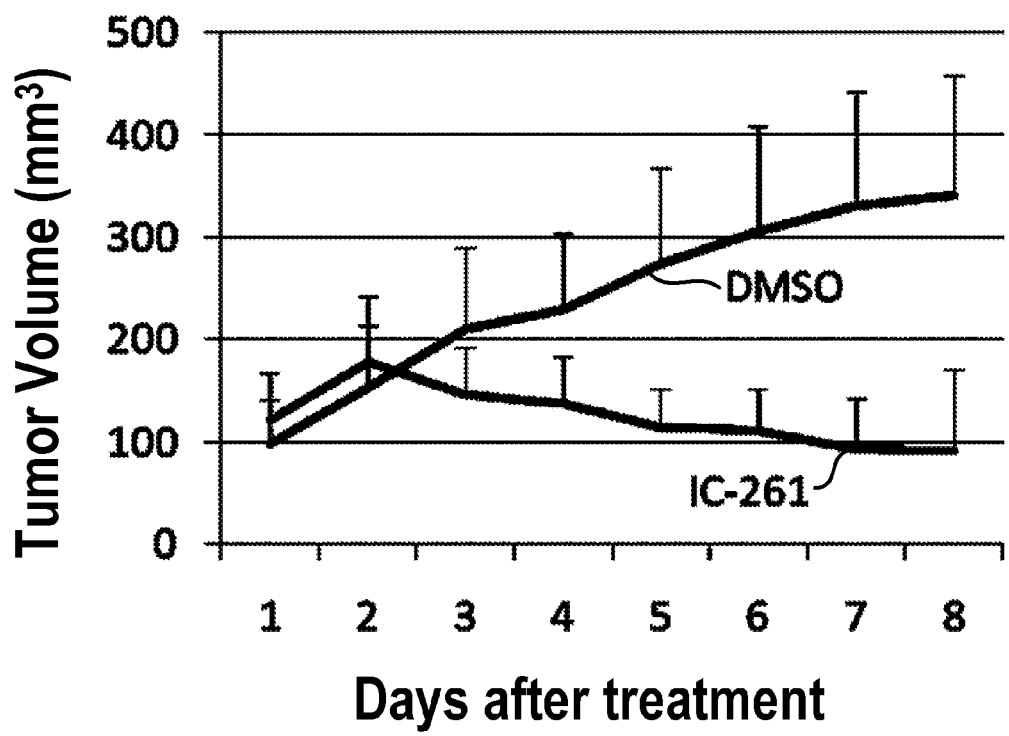
FIG. 7A graphically illustrates that IC261 treatment inhibits growth of IMR-32 (amplified MYCN expression) xenograft tumors in vivo in comparison to DMSO control treatment; as described in Example 2.
Figure 7B:
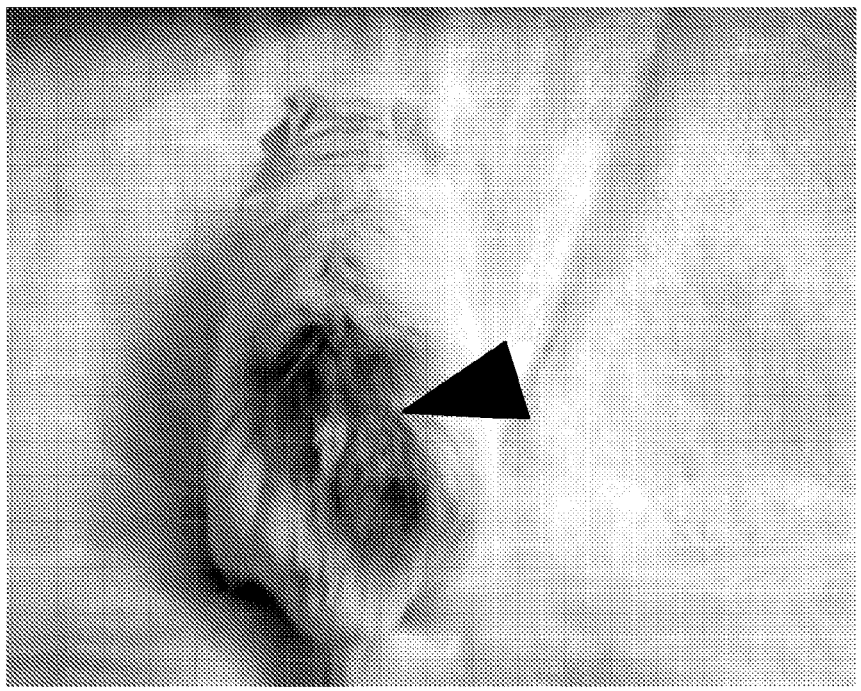
FIG. 7B shows a xenograft mouse before and after treatment with IC261; as described in Example 2.
Figure 7B:
Figure 7C:
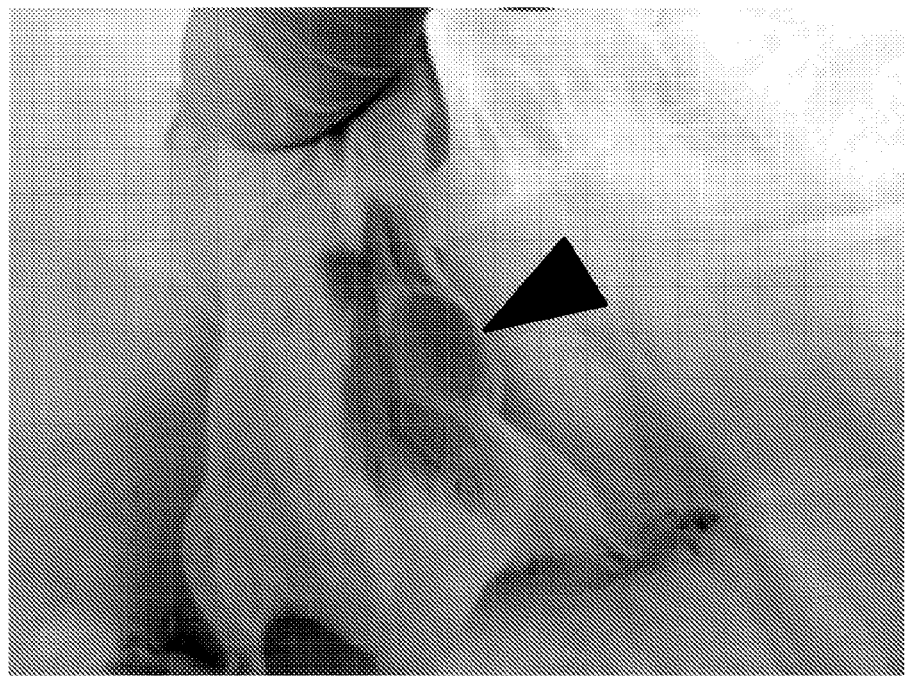
FIG. 7C shows a xenograft mouse before and after treatment with DMSO (control); as described in Example 2.
Figure 7C:
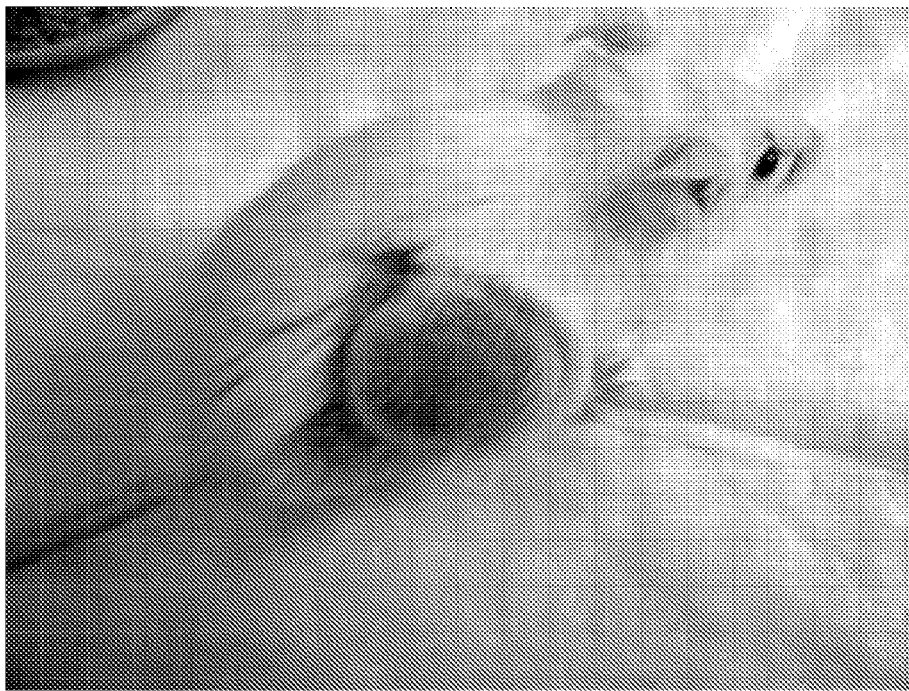
Figure 7D:
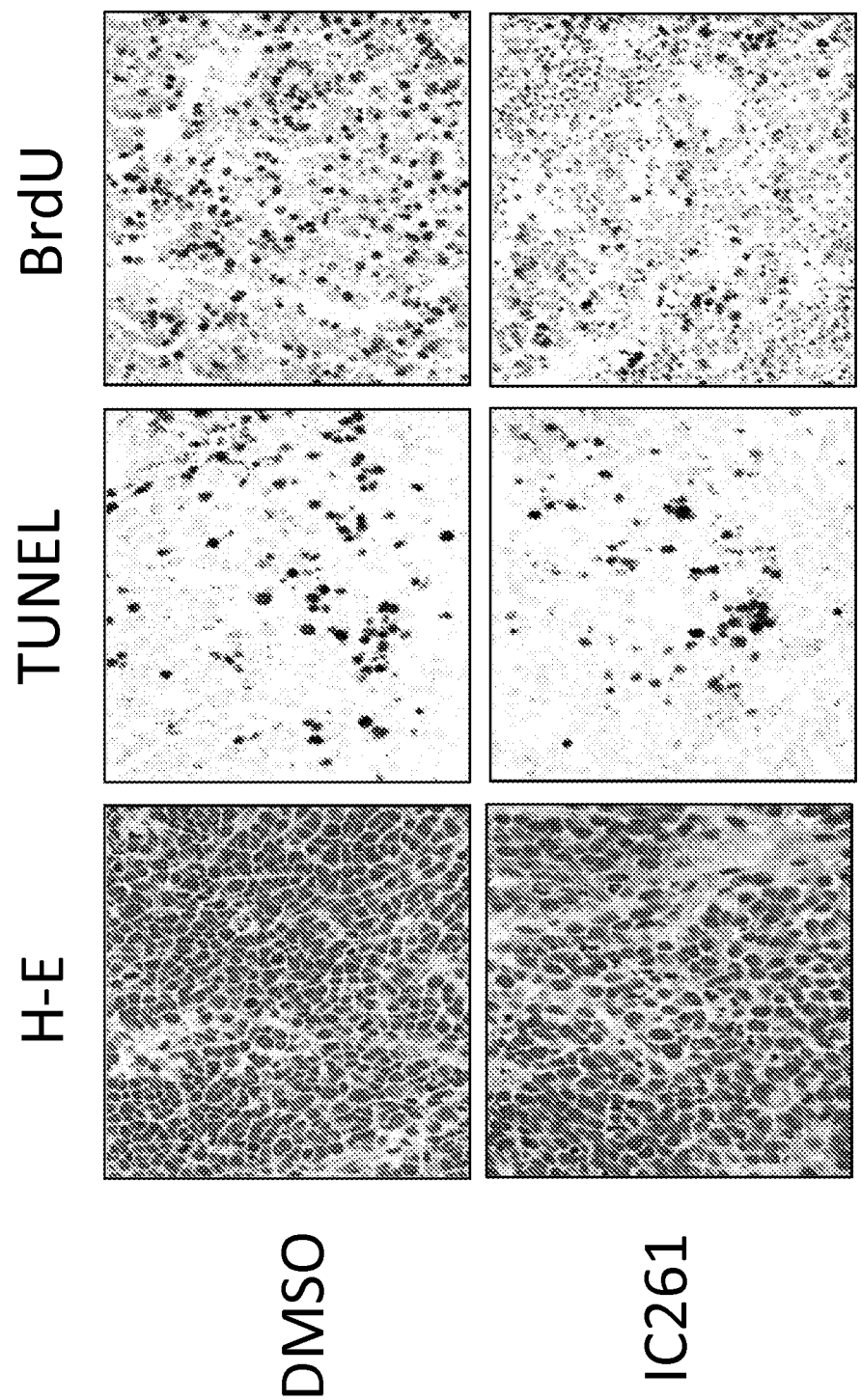
FIG. 7D shows immunohistochemical analysis of tumor sections from IC261 and DMSO treatment groups stained with H-E, TUNEL or BrDu; as described in Example 2.

To evaluate the therapeutic potential of CSNK1ε kinase inhibitors, IC261, a small molecule inhibitor of CSNK1ε and d kinase activity (Mashhoon, N., et al., "Crystal Structure of a Conformation-Selective Casein Kinase-1 Inhibitor," *J Biol Chem* 275:20052-20060, 2000) was administered to mice with established IMR-32 (amplified MYCN expression) xenograft blastoma tumors. Specifically, 10 NOD/SCID mice were injected with 1×10$^7$ IMR-32 blastoma cells. The tumors were allowed to establish for 6 weeks. The mice were randomized into control and IC261 treatment groups. At the start of treatment, the average tumor size for the control mice was 98.8±42.5 mm$^3$, whereas the average tumor size for the IC261 treatment group was 121.9±46.9 mm$^3$. The groups were subcutaneously injected once daily for seven days with 20.5 mg/kg of IC261 or DMSO in 200 µl. During treatment, the tumor size was monitored. As illustrated in FIG. 7A, during the first two days of treatment, there was no significant difference in tumor volume between the DMSO and IC261-treated mice. However, at day three the average tumor volume of the IC261-treated mice was reduced, a trend that continued throughout the remaining treatment schedule, ultimately to a volume of about 100 mm$^3$. In contrast, the tumor volume of the DMSO-treated mice continued to increase to a volume of about 350 mm$^3$. Photographs of a representative mouse from the IC261 and control groups, before and after treatment, are shown in FIGS. 7B and C, respectively. Histological sections of tumors from each group were prepared after the 8th day of IC261 treatment. The tumor sections were subjected to hematoxylin and eosin (H-E) stain, TUNEL stain, and BrdU staining to ascertain the cell structure, and frequencies of cell apoptosis, and cell proliferation within the tumors. As shown in FIG. 7D, the IC261-treated tumor has drastically reduced indications of cell proliferation in the BrdU stain in comparison to the control (DMSO-treated) tumor. The images shown in FIG. 7D are representative of at least 10 fields viewed over two stained sections per animal.

Conclusion

This Example demonstrates that the reduction of CSNK1ε expression and/or enzymatic activity, whether by expression knockdown or chemical inhibitor of the kinase domain, was effective to inhibit the growth and proliferation of cancer cells and reduced the tumor size of MYC-driven neuroblastoma cancers. These results validate CSNK1ε as a therapeutic target for MYC-driven cancers.

Example 3

This Example describes a method for determining the functional status of WNT activity in neuroblastoma cells, and methods for screening for inhibitors of CSNK1ε.

Rationale

As described in Example 1, high expression of CSNK1ε was found to correspond with amplified expression of MYC oncogene in tumor cells and selective inhibition of CSNK1ε expression or kinase activity was found to result in reduced viability of neuroblastoma cells with amplified MYCN expression. Further, as described in Example 2, selective inhibition of CSNK1ε expression or kinase activity in neuroblastoma xenografts with amplified MCYN expression was found to result in a reduction in tumor size in vivo. To better understand the functional mechanisms that drive the relationship between CSNK1ε and MYC oncogenes, the role of CSNK1ε in two developmental pathways was investigated with reference to MYC expression.

Methods and Results

CSNK1 Knock-Down Influences Two Developmental Pathways, WNT and SHH.

Figure 8A:
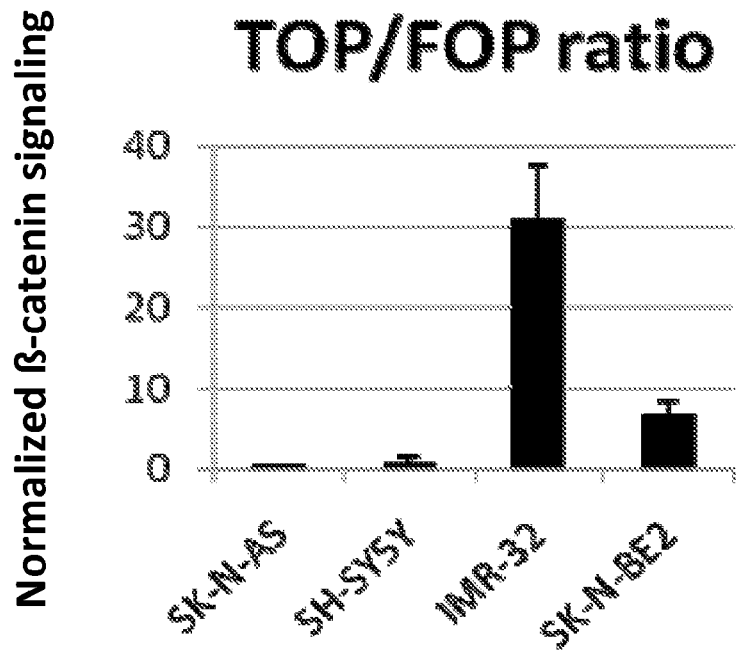
FIG. 8A is a bar graph illustrating that WNT mediated transcriptional response was markedly elevated in neuroblastoma cells with amplified MYCN expression compared to neuroblastoma cells with normal MYCN expression, wherein WNT signaling is expressed as a function of detectable β-catenin reporter signaling; as described in Example 3.

CSNK1ε has been implicated as a positive regulator of WNT signaling (Sakanaka, C., "Phosphorylation and Regulation of Beta-Catenin by Casein Kinase I Epsilon," *J Biochem* 132:697-703, 2002). To determine the functional status of WNT activity in neuroblastoma cells with or without amplified MYCN expression, a WNT dual reporter system, employing both consensus (TOP) and mutant (FOP) TCF binding sites was assayed in neuroblastoma cell lines SK-N-AS (MYCN not amplified), SH-Sy5Y (MYCN not amplified), IMR-32 (MYCN amplified and overexpressed), and SK-N-BE2 (MYCN amplified and overexpressed), as described in (Biechele, T. L., et al., "Transcription-Based Reporters of Wnt/beta-Catenin Signaling," *Cold Spring Harb Protoc* 2009, pdb prot5223). As illustrated in FIG. 8A, WNT mediated transcriptional response was markedly elevated in cells with MYCN amplification, (i.e., IMR-32 and SK-N-BE4), as indicated by β-catenin signaling.

Figure 8B:
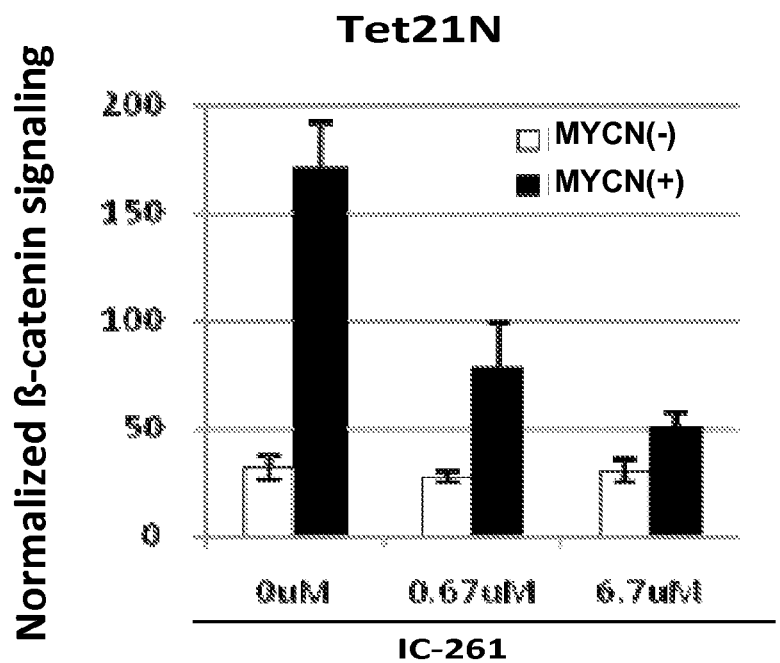
FIG. 8B is a bar graph of WNT signaling as a function of IC261 treatments in neuroblastoma cells that express inducible Tet-MYCN, wherein WNT signaling is expressed as a function of detectable β-catenin reporter signaling; as described in Example 3.

A potential direct connection of WNT with MYCN expression was explored utilizing neuroblastoma cells expressing an inducible Tet-MYCN gene. Tet-21N neuroblastoma cells (normal MYCN expression) carrying a Tet-off-MYCN gene, were treated with or without Dox (a tetracycline compound), as described supra. Western blot analysis indicated that Tet-MYCN cells receiving Dox lowered CSNK1ε expression in parallel with repression of the levels of MYCN as compared to the no-Dox cells (data not shown). Further, the WNT activity was assayed through the detectable activity of an integrated WNT reporter. As illustrated in FIG. 8B, the neuroblastoma cells with MYCN-on expression had highly elevated WNT signaling, as indicated by detectable β-catenin signal and the addition of IC-261 resulted in the repression of the WNT reporter. These results suggest that MYCN may exert a positive feedback on WNT in neuroblastoma, which is consistent with the previous report that c-MYC overexpression positively affects WNT in breast cancer cells (Cowling, V. H., and M. D. Cole, "Turning the Tables: Myc Activates Wnt in Breast Cancer," *Cell Cycle* 6:2625-2627, 2007).

The conditional knock-down of CSNK1ε using the Dox-inducible lentiviral constructs described supra also lowered the activity of an integrated WNT reporter in neuroblastoma cells (data not shown). This indicates that CSNK1ε activity mediates the MYCN effect on WNT signaling activity.

Figure 8C:
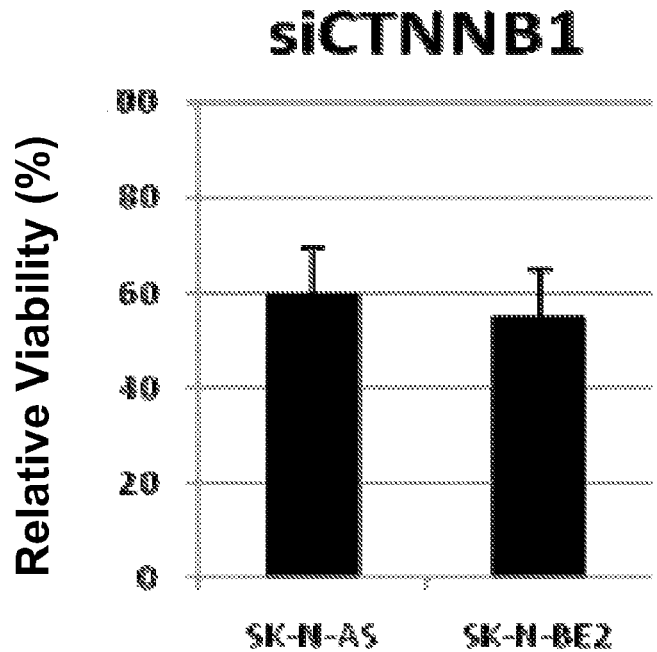
FIG. 8C is a bar graph demonstrating that transient knock-down of β-catenin similarly affected viability of neuroblastoma cells with or without amplified MYCN expression; as described in Example 3.

However, it is noted that knock-down of a key mediator of WNT signaling, β-catenin, using a siRNA construct ("siCTNNB1") had equivalent affects on the viability of SK-N-AS and SK-N-BE2, neuroblastoma lines with non-amplified MYCN and amplified MYCN, respectively. See FIG. 8C. These results suggested that the selective growth inhibition caused by CSNK1ε knockdown may be caused by both WNT-dependent and independent effects.

Figure 8D:
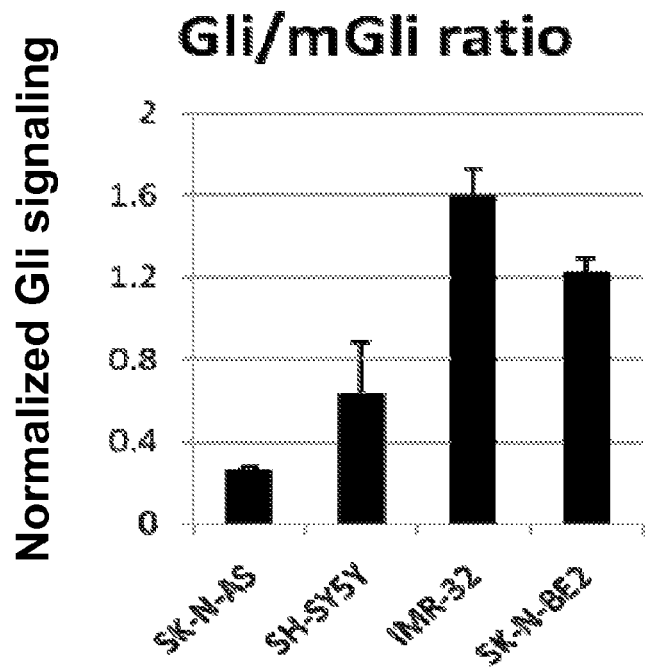
FIG. 8D is a bar graph illustrating the Sonic Hedgehog (SHH) signaling in neuroblastoma cells with amplified MYCN expression (IMR-32 and SK-N-BE2) and without amplified MYCN expression (SK-N-AS and SH-Sy5Y), wherein SHH signaling is illustrated as a function of Gli/mGLi signaling ratio; as described in Example 3.

To delineate at a global level the effects of CSNK1ε knock-down, microarray analysis of mRNA isolated after conditional silencing of CSNK1ε was carried out in SK-N-BE2 neuroblastoma cells (MYCN amplified and overexpressed) and compared with samples transduced with a control lentiviral vector. The results indicated significant changes in gene expression of a broad set of genes. Pathway analysis of the down-regulated genes revealed that several were implicated in Sonic Hedgehog ("SHH") signaling. This indicated that the SHH developmental pathway plays a role in the cellular response to CSNK1ε knock-down. To verify SHH involvement in neuroblastomas with MYCN amplification, a GLI dual reporter system was assayed in neuroblastoma cell lines according to the method previously described in Sasaki, H., et al., "A Binding Site for Gli Proteins Is Essential for HNF-3beta Floor Plate Enhancer Activity in Transgenics and Can Respond to Shh in vitro," *Development* 124:1313-1322, 1997. GLI1 is the downstream transcription factor that mediates SHH response and reporters carrying GLI1 binding sites are utilized to measure the status of the pathway. As illustrated in FIG. 8D, high Gli/mGli ratios were observed in IMR-32 and SK-N-BE2 neuroblastoma lines (both with amplified MYCN expression) versus SK-N-AS and SH-SY5Y neuroblastoma lines (both with normal MYCN expression), indicating high SSH reporter levels in the neuroblastomas with amplified MYCN expression.

Figure 8E:
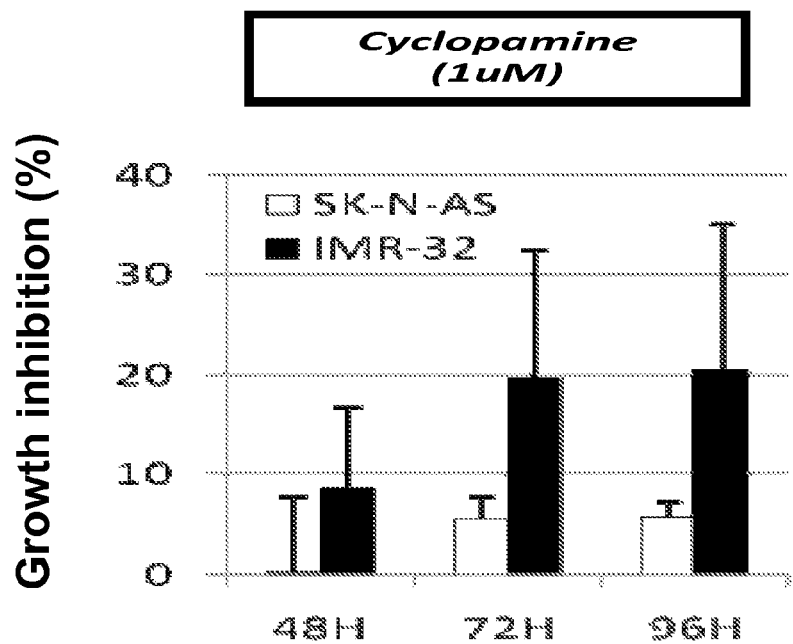
FIG. 8E is a bar graph that illustrates the inhibitory effect of SHH inhibitor cyclopamine on the growth of neuroblastoma calls with amplified MYCN expression (IMR-32) and without amplified MYCN expression (SK-N-AS), wherein cells were incubated with 10 μM cyclopamine; as described in Example 3.
Figure 8F:
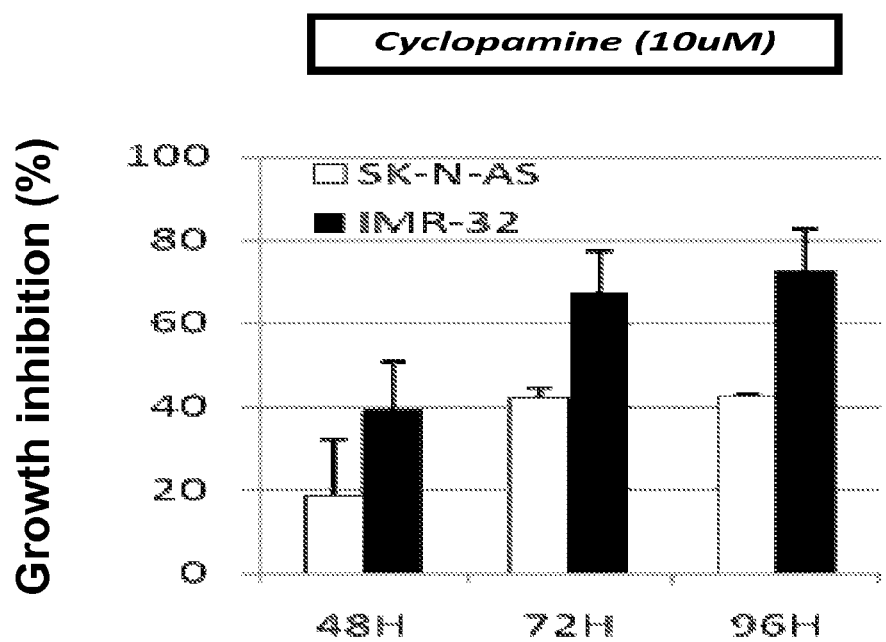
FIG. 8F is a bar graph that illustrates the inhibitory effect of SHH inhibitor cyclopamine on the growth of neuroblastoma calls with amplified MYCN expression (IMR-32) and without amplified MYCN expression (SK-N-AS), wherein cells were incubated with 10 μM cyclopamine; as described in Example 3.

Cyclopamine, a known natural inhibitor of SHH, was administered to SK-N-AS and IMR-32, to assess the impact of SHH inhibition on cell viability of neuroblastoma cells with normal and amplified MYCN expression, respectively. Cyclopamine was administered to the SK-N-AS and IMR-32 in 1 µM or 10 µM doses, and the growth inhibition was assayed at 48, 72 and 96 hours. Growth inhibition was detected in both neuroblastoma cell types. However, the effect was more pronounced in neuroblastoma cells with amplified MYCN expression (IMR-32). See FIGS. 8E and F. Combined, these data indicate a dependence of MYC over-expressing cells on a functional SHH signaling pathway and its interaction with CSNK1ε function.

Conclusion

These results indicate that CSNK1ε influences both WNT and SHH signaling through a potential positive feedback loop set up by MYCN amplification. The activity of both pathways appears to contribute to the proliferative potential neuroblastomas that overexpress of MYCN.

Example 4

This Example demonstrates the use of inhibitors of CSKN1ε to inhibit proliferation of ovarian cancer cells in vitro and in vivo.

Rationale

As described in Examples 1-2, elevated expression of CSNK1ε was found to correlate with amplified expression of MYCN in neural cancer cells. As demonstrated in Example 1 and 2, reduction of CSNK1ε in cancer cells with amplified MYCN expression reduced the viability of the cells, both in vitro and in vivo. Further, as described in Example 3, the proliferative effects of CSNK1ε on neuroblastoma cells with amplified MYCN expression are likely mediated by WNT and SHH signaling, which provides a positive feedback on the regulation of CSNK1ε. To assess whether CSNK1ε plays a similar role for other isotypes of MYC in non-neural cancers, expression of CSNK1ε was manipulated in ovarian cancer cells that exhibited amplified MYC expression.

Methods and Results

Characterization of ovarian cancer lines for c-MYC expression status.

Six human ovarian cancer cell lines were characterized for their relative expression levels of c-MYC as follows. First, a Western blot was performed using protein extractions obtained from the ovarian cancer cell lines CaOV3, RMG-1, DOV-13, PE04, IGROV-1, and TOV112D. The protein extractions were separated by SDS-PAGE, blotted and probed with a c-MYC monoclonal antibody (sc-42 and sc-764, Santa Cruz Biotechnology) under stringent hybridization conditions.

Figure 9A:
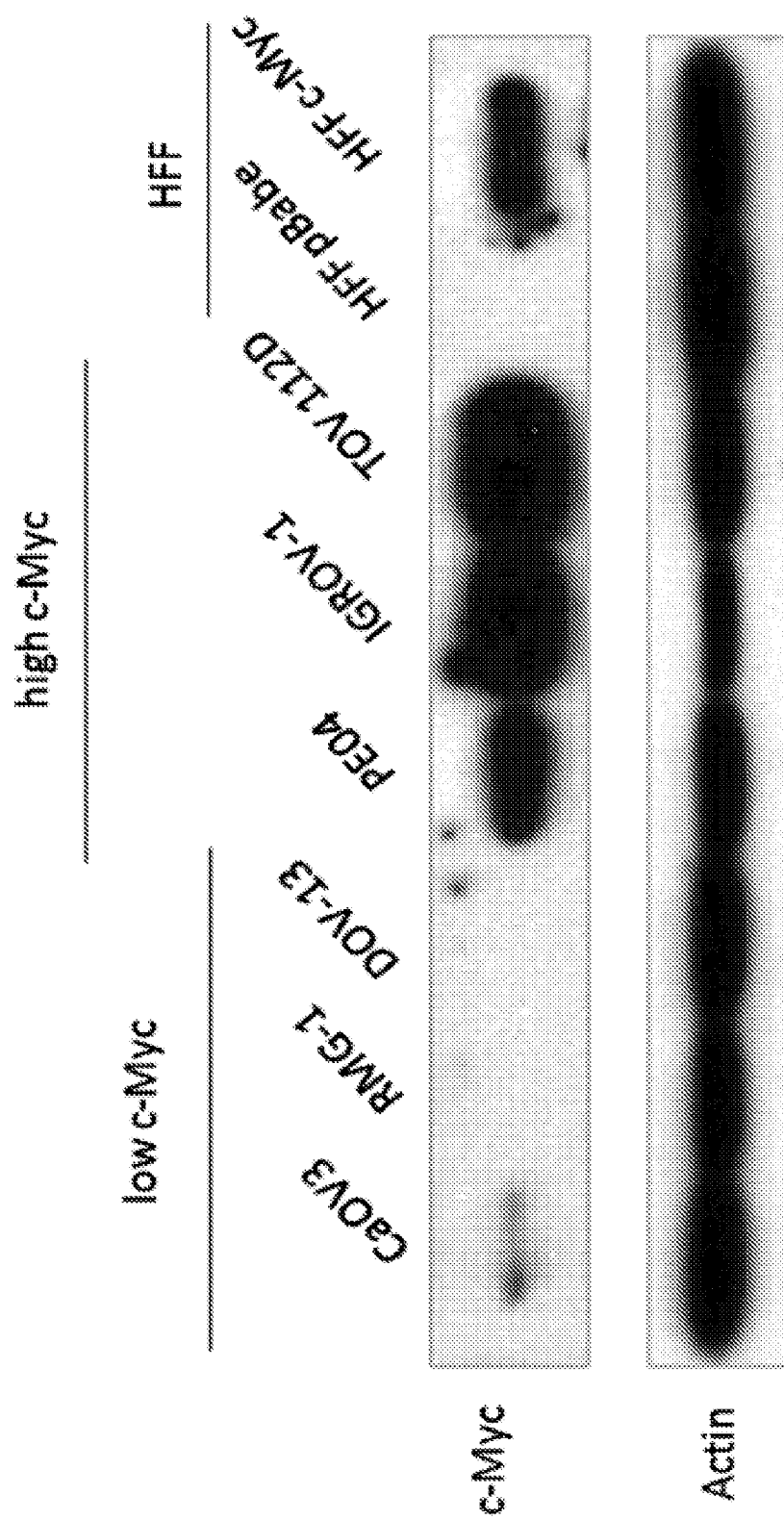
FIG. 9A is a Western blot illustrating relative levels of c-MYC protein in several ovarian cancer cell lines; as described in Example 4.

As illustrated in FIG. 9A, the Western blot revealed high levels of cMYC in PE04, and especially in IGROV-1 and TOV112D cell lines. In contrast, the Western blot revealed low c-MYC levels in CaOV3 cells, and no detectable c-MYC in RMG-1 and DOV-13 ovarian cancer cell lines. As a control, human foreskin primary cells (HFF with control vector pBabe) that express low levels of c-MYC were used as a negative control, and HFF cells with a c-MYC transgene was used as a positive control.

Figure 9B:
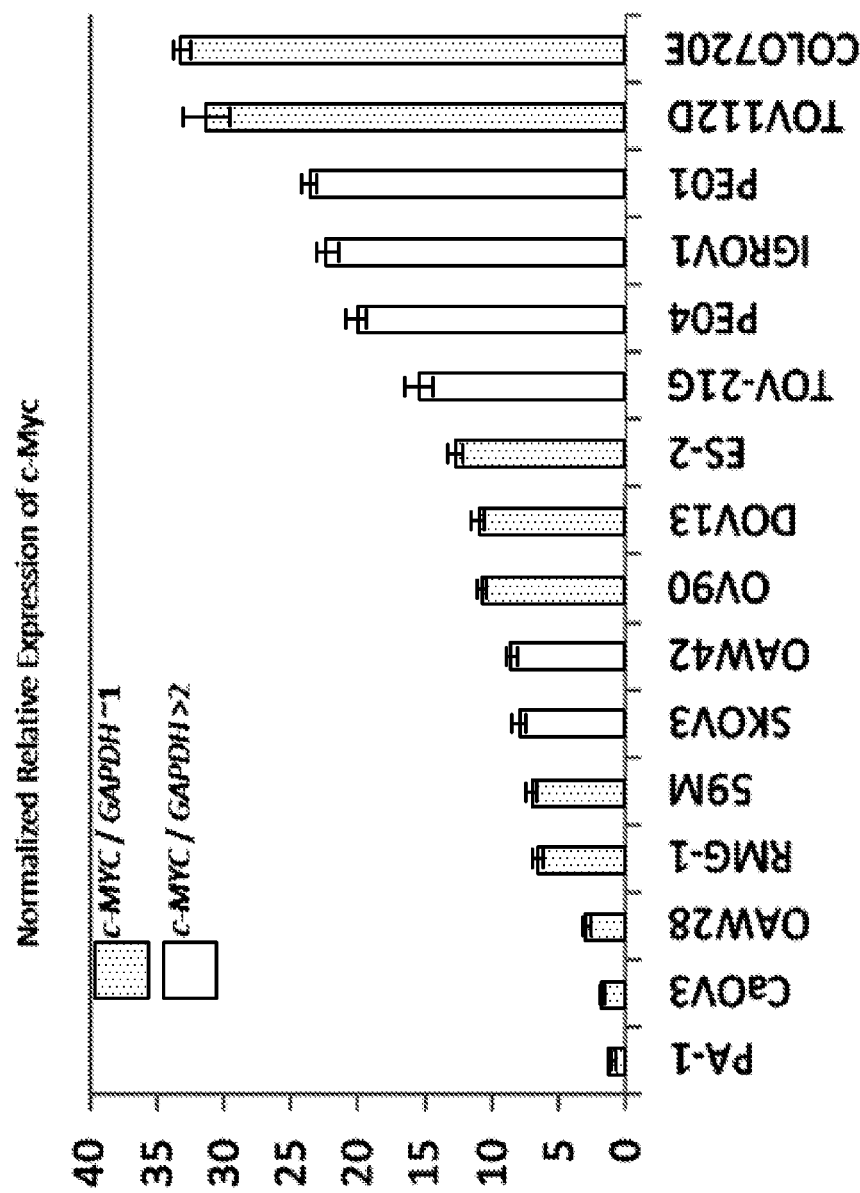
FIG. 9B is a bar graph illustrating the relative expression levels of c-MYC mRNA in several ovarian cancer cell lines as determined by qRT-PCR analysis; as described in Example 4.

Second, c-MYC mRNA was quantified in various ovarian cancer cell lines using quantitative RT-PCR. The expression levels of c-MYC were normalized to the detected levels of the reference standard gene, GAPDH. FIG. 9B illustrates the normalized c-MYC mRNA levels in increasing order. Spotted bars indicate cell lines with an approximate single gene copy of GAPDH, whereas open boxes represent cell lines with multiple gene copies of the standard gene. It is noted that the cell lines PE04, IGTOV-1 and TOV112D, previously identified by the Western blot assay as having elevated levels of c-MYC polypeptide, are among the ovarian cell lines with the highest mRNA levels for c-MYC.

Figure 9C:
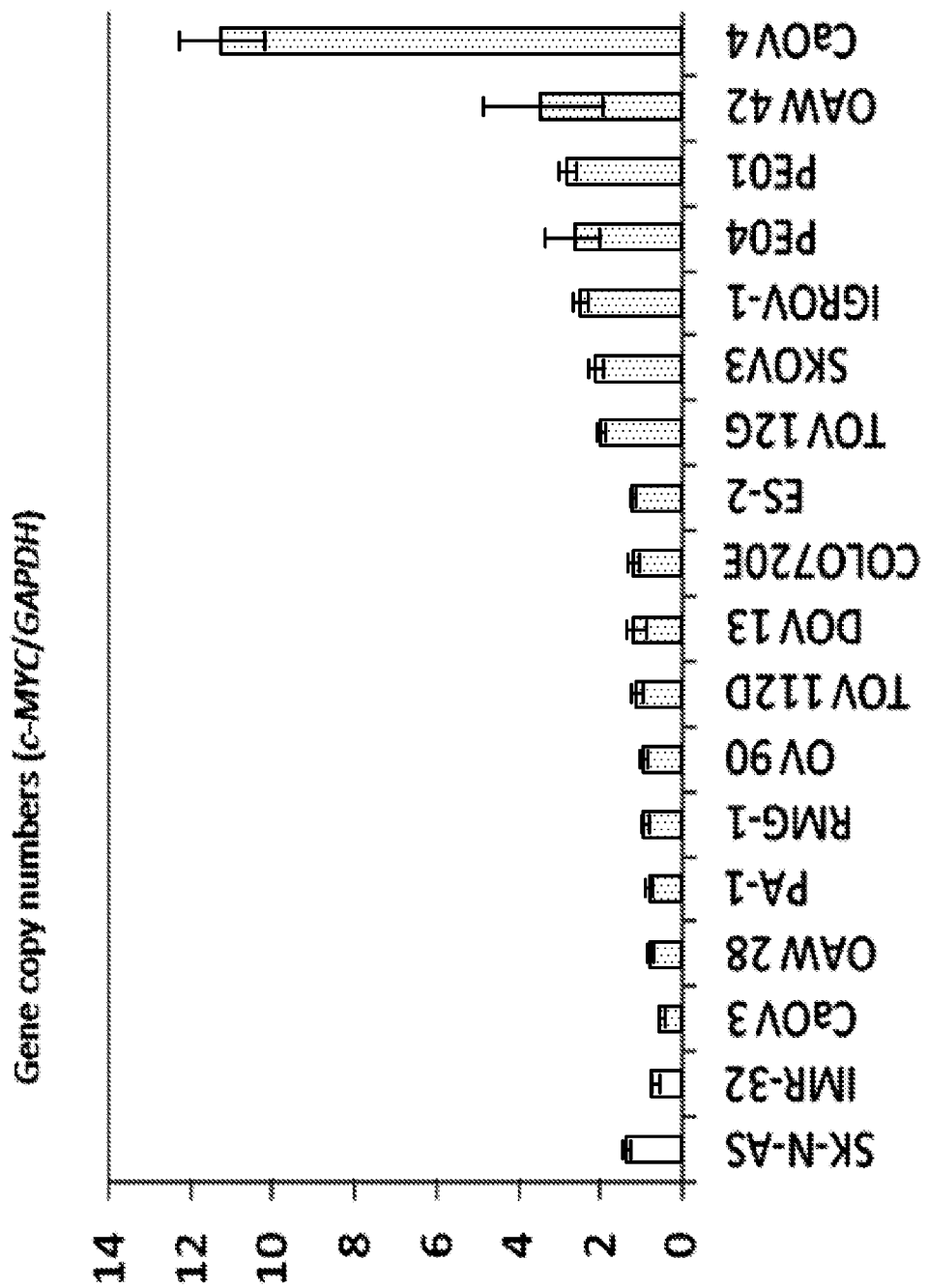
FIG. 9C is a bar graph illustrating the gene copy number of c-MYC in several ovarian cancer cell lines as determined by PCR analysis; as described in Example 4.

Third, because many transformed cells exhibiting MYC-driven overexpression and therefore MYC-driven proliferation are known to have experienced duplications in the MYC gene, the copy number of c-MYC was assessed by PCR in the ovarian cancer cell lines. The copy number of the various assayed ovarian cancer cell lines are represented in FIG. 9C as a function of GAPDH copy number. It is noted that IGROV-1 and PE04, which were previously identified as having amplified c-MYC expression have increased copy numbers of the c-MYC gene. The TOV112D cell line, however, does not appear to have increased c-MYC copies, which indicates that the amplified expression levels of the gene in these cells results from de-regulated transcription from a single gene locus.

Knockdown of CSNK1 Expression in Ovarian Cancer Cells with Amplified c-MYC.

siRNAs targeting CSNK1ε were transfected into two ovarian cancer cell lines with amplified c-MYC expression (IGROC-1 and TOV112D) and two ovarian cancer cell lines with normal, (i.e., low, non-amplified), expression levels of c-MYC (CaOV3 and DOV13) to induce transient knock-down of the CSNK1ε gene. siRNAs targeting UNI served as the negative control and siRNAs targeting KIF11, which is toxic to all cells, served as the positive control. Cell viability was assayed using the Cell Titer Glow Assay at five days post-transfection. The relative viability of the IGROV-1 and TOV112D cell lines were reduced to approximately 55% and 40%, respectively. In contrast, the relative viability of the CaOV3 and DOV13 cell lines were reduced to approximately 95% and 85%, respectively. This data indicates that CSNK1ε is necessary for the viability of ovarian cancer cells that exhibit amplified c-MYC expression.

Figure 10A:
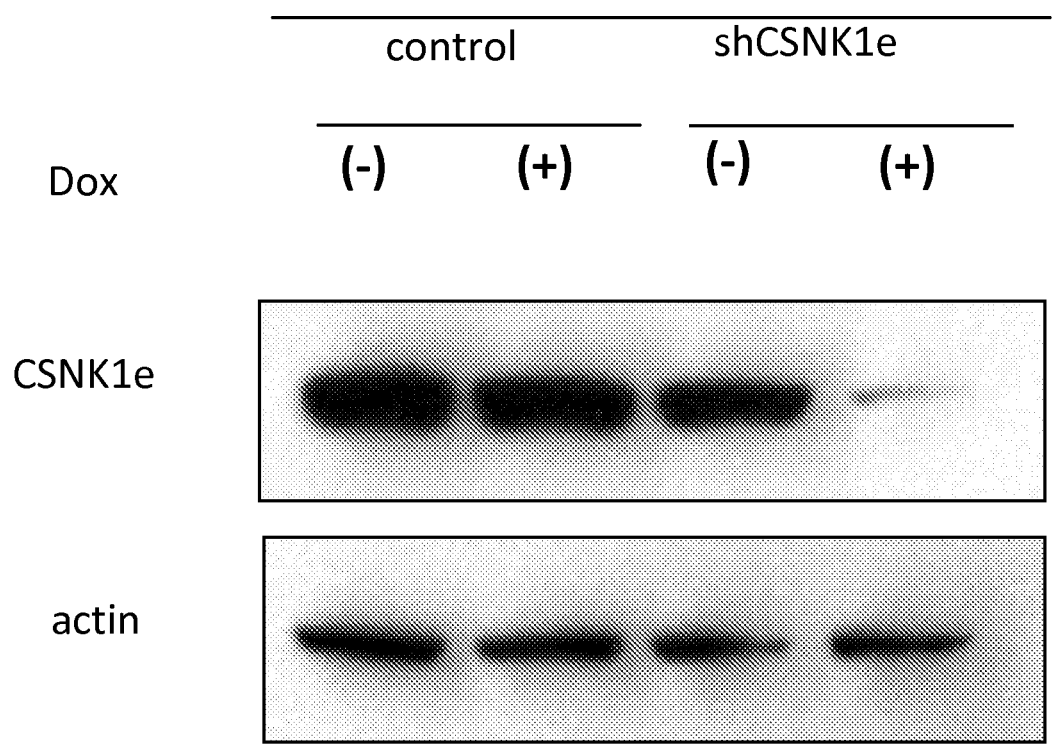
FIG. 10A is a Western blot demonstrating knock-down of CSNK1ε using lentivirus construct encoding Dox-induced shRNA transfected in ovarian cancer cells with amplified c-MYC expression (COLO720E); as described in Example 4.
Figure 10B:
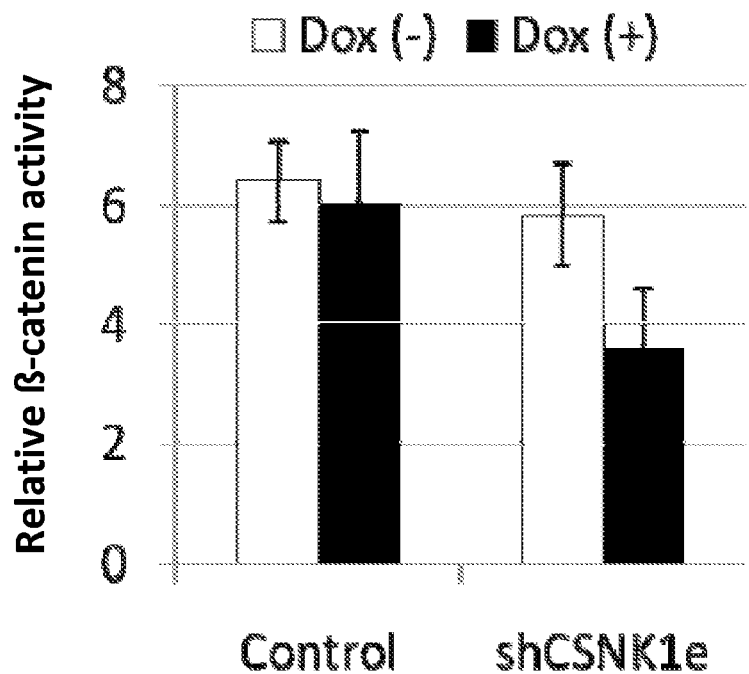
FIG. 10B is a bar graph illustrating that inducible shRNAi knock-down of CSNK1ε in ovarian cancer cells with amplified c-MYC expression (COLO720E) causes a decrease in WNT signaling, wherein WNT signaling is measured as a function of β-catenin reporter signaling; as described in Example 4.
Figure 10C:
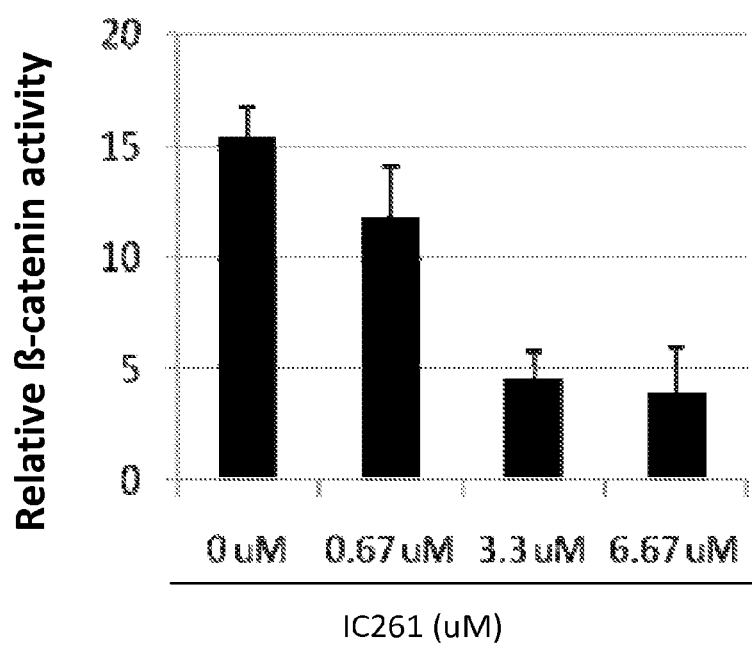
FIG. 10C is a bar graph illustrating that inhibition of CSNK1ε kinase function in ovarian cancer cells with amplified c-MYC expression (COLO720E) cultured with increasing doses of IC261 causes a decrease in WNT signaling, wherein WNT signaling is measured as a function of β-catenin reporter signaling; as described in Example 4.

The impact of stable knock-down of CSNK1ε was assessed for the expression for WNT signal function. To confirm the efficacy of the stable knockdown technique in ovarian cells, Dox-inducible lentivirus constructs encoding shRNAs targeting CSNK1ε were transduced into COLO720E ovarian cells. It is noted that this cell line exhibited the highest c-MYC mRNA levels of all the ovarian cancer cell lines. See FIG. 9B. As illustrated in FIG. 10A, induction of transduced cells with Dox resulted in a drastic reduction in CSNK1ε polypeptide levels, compared to uninduced cells or cells with control lentiviral constructs. Next, to assess the WNT signaling activity, relative O-catenin activity was assayed as described, supra, for COLO720E ovarian cells transduced with the shRNA encoding lentivirus targeting CSNK1ε. Upon Dox induction, the relative β-catenin activity was reduced by approximately one third compared to the uninduced cells. A similar effect on relative β-catenin activity was observed upon administration of IC261, the inhibitor of CSNK1ε. Briefly, COLO720E cells were cultured in 0, 0.67, 3.3, and 6.67 μM IC261. As illustrated in FIG. 10C, the relative β-catenin activity, hence WNT signaling, was reduced by more than two thirds at the higher doses of IC261. This indicates that, similar to the results in neuroblastomas, the effect of CSNK1ε on viability of ovarian cancer cells with amplified c-MYC expression is likely mediated by the WNT signaling pathway.

Inhibition of CSNK1ε by IC261 Selectively Impairs Growth of Ovarian Cancer Lines with Amplified c-MYC.

The effect of CSNK1ε on the cell viability of ovarian cancer lines was investigated in vitro. First, HFF (non-cancer primary cells) with control vector, RMG-1 (normal c-MYC expressing), CaOV3 (normal c-MYC expressing), HFF with cMYC induced (amplified c-MYC expressing), TOV112D (amplified c-MYC expressing), and COLO720E (amplified c-MYC expressing) were exposed to increasing concentrations of IC261. Cell viability was assessed as described above. At 0.5 log μM and above, all of the cells with amplified c-MYC exhibited drastic reduction of relative viability to 25% or less, whereas the normal c-MYC expressing cells exhibited cell viabilities of approximately 75% and above.

Similar assays were performed with an additional panel of ovarian cancer cells, including IGROV-1, PE01, DOV13, OAW42, TOV21G, and SKOV3. The log of the half maximal effective concentration (log $IC_{50}$) was calculated to reflect half the concentration of IC261 required to results in complete loss of cell viability. The results are provided below in Table 2. Notably, IGROV-1 and PE01, two ovarian cancer cell lines previously established as having some of the highest c-MYN expression levels had the highest log $IC_{50}$ values, indicating a high potency of IC261 to cause a reduction in cell viability.

TABLE 2

The log of the half maximal inhibitory concentration of IC261 to results in complete loss of cell viability for select ovarian cancer cell lines.

| Cell | log $IC_{50}$ | log $IC_{50}$ 95% Confidence Intervals |
| --- | --- | --- |
| IGROV-1 | 2.767 | 1.924-3.609 |
| PE01 | 0.9447 | 0.6665-1.223 |
| DOV13 | 0.8505 | 0.6573-1.044 |
| OAW42 | 0.8204 | 0.6288-1.012 |
| TOV21G | 0.8162 | 0.6273-1.005 |
| SKOV3 | 0.6656 | 0.4959-0.8354 |

Figure 11A:
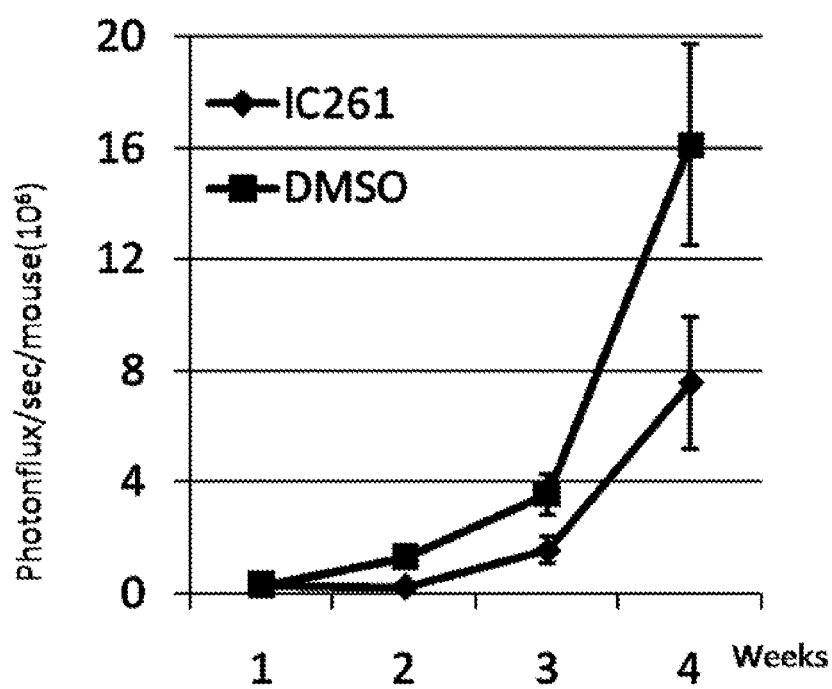
FIG. 11A graphically illustrates the reduction of cancer cell proliferation and viability in mice containing intraperitoneal xenografts of human ovarian cancer cells (TOV112D/Luc) after treatment with IC261 or DMSO control, wherein cancer cell proliferation and viability is determined by Luc imaging; as described in Example 4.
Figure 11B:
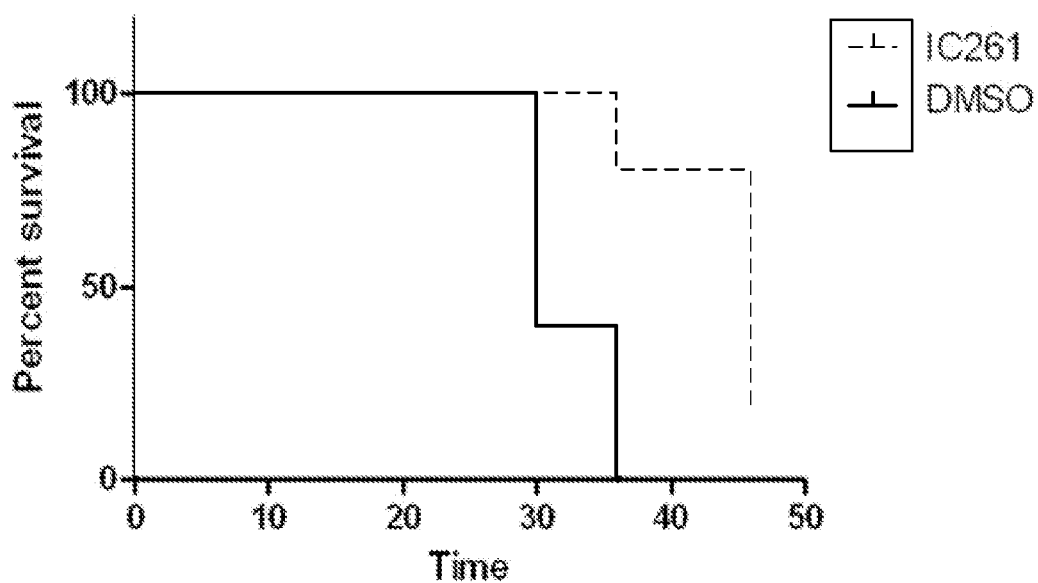
FIG. 11B is a Kaplan-Meier survival plot illustrating improved survival rate after treatment with IC261 in mice containing intraperitoneal xenografts of human ovarian cancer cells; as described in Example 4.

The effect of CSNK1ε on the cell viability of ovarian cancer cells was then investigated in vivo. Peritoneal carcinomatosis model mice were generated by the intraperitoneal injection of TOV112D/Luc cells. After one week, the mice were randomized into control and experimental groups, which then received daily injections of IC261 or DMSO carrier for three weeks. Weekly Luc imaging was performed for each mouse at the termination of each week of the experiment to monitor the relative viability of cancer cells that have established in the mice. As illustrated in FIG. 11A, mice receiving daily IC261 injections exhibited significantly reduced cancer cell proliferation and viability after two weeks compared to mice receiving DMSO. The difference among treatment groups was much more pronounced by week four. As illustrated in the survival graph in FIG. 11B, the DMSO group and IC261 treatment groups diverged in percent survival starting at day 30 when the DMSO group began to experience drastic mortality. This demonstrates that the inhibition of CSNK1ε reduced the viability of ovarian cancer cells with amplified expression in vitro. Moreover, the inhibition of CSNK1ε in ovarian cancer in vivo resulted in reduced cancer cell viability and proliferation, and ultimately prolonged the life of the subjects.

Analysis of CSNK1ε Inhibitor on the Progression of the Cell Cycle.

Figure 12A:
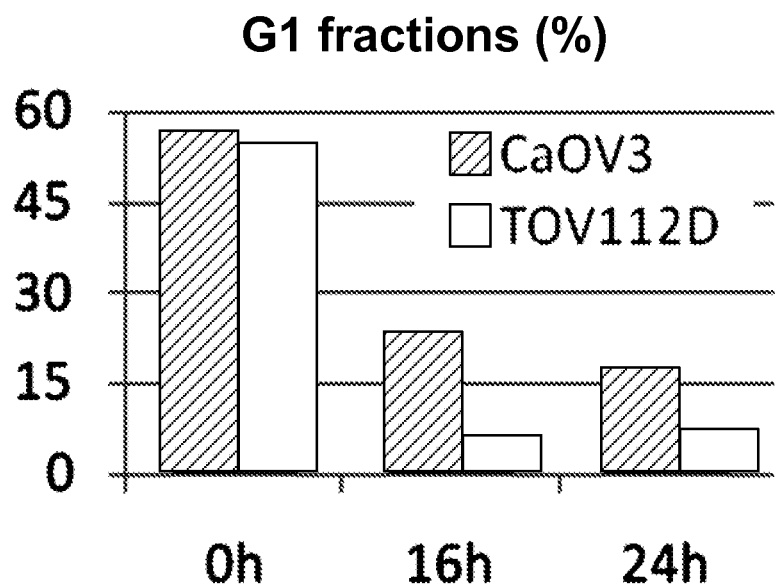
FIG. 12A graphically illustrates the fraction of ovarian cancer cells with amplified c-MYC expression (TOV112D) and without amplified c-MYC expression (CaOV3) at the G1 checkpoint of the cell cycle before and after administration of 1 μM IC261; as described in Example 4.
Figure 12B:
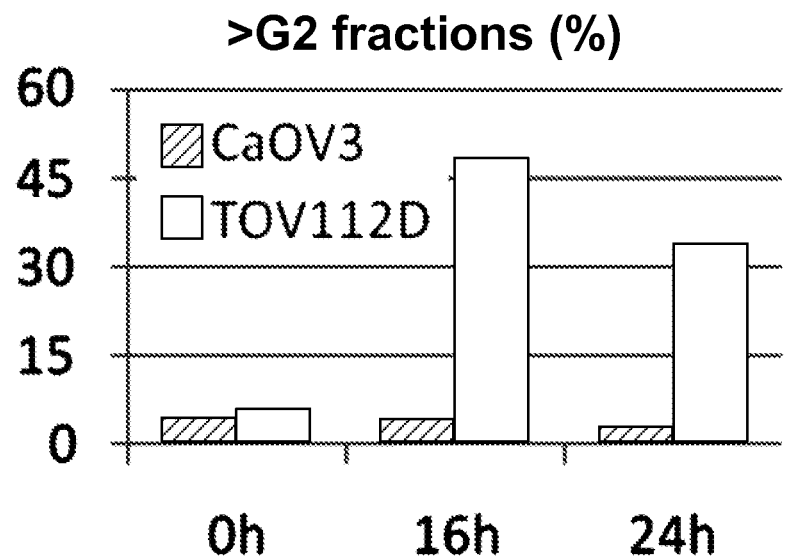
FIG. 12B graphically illustrates the fraction of ovarian cancer cells with amplified c-MYC expression (TOV112D) and without amplified c-MYC expression (CaOV3) at the G2 checkpoint of the cell cycle before and after administration of 1 μM IC261; as described in Example 4.

Ovarian cancer cell lines with normal (i.e., low) and amplified expression of c-MYC were assessed for the impact of the CSNK1ε inhibitor IC261 on the progression of the cell cycle. CaOV3 cells (normal c-MYC expression) and TOV112D cells (amplified c-MYC expression) were cultured in 1 μM IC261. The cells were assessed for the state of the cell cycle, namely G1, S-phase, and G2, at time points before and 16 and 24 hours after contact with IC261 by Propidium Iodide staining followed by FACS analysis. As illustrated in FIG. 12A, the majority of cells from both cell lines were in the G1 phase of the cell cycle before treatment of IC261. After administration of IC261, the percentage of cells in the G1 phase was drastically reduced. However, the levels were lower for the cells with amplified c-MYC expression. In contrast, very few cells from either cell line were observed in the G2 phase before administration of IC261. See FIG. 12B. Upon administration of IC261, however, a large fraction of the cancer cells with amplified c-MYC expression were arrested at the G2 checkpoint. This trend was not observed for the cancer cells with normal c-MYC expression. This indicates that CSNK1ε function is required for progression of MYC-driven cancer cells to progress from the G2 checkpoint into metaphase. In contrast, for normal c-MYC ovarian cancer cells IC261 only has a small and transient ability to cause cell cycle arrest in G2.

Role of CSNK1ε Inhibitor in Sensitivity of Ovarian Cancer Cells to Treatment with Cisplatin.

Figure 13A:
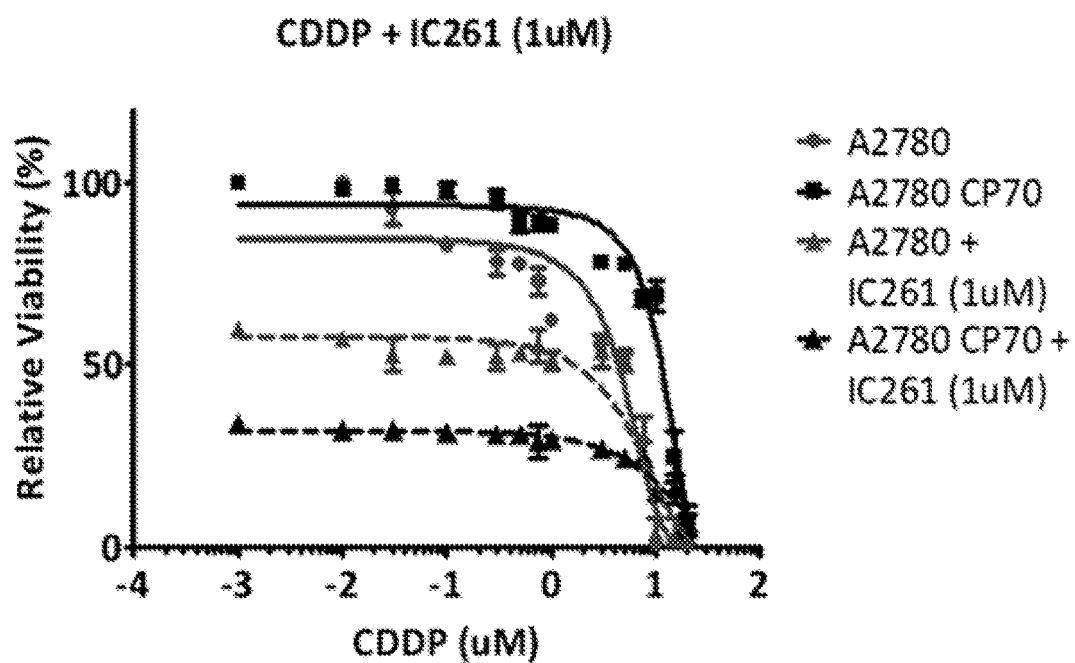
FIG. 13A graphically illustrates the relative cell viability of A2780 and A2780-CP70 (cisplatin-resistant) ovarian cancer cells in the presence of increasing doses of cisplatin (CDDP) when cultured in the presence of IC261; as described in Example 4.
Figure 13B:
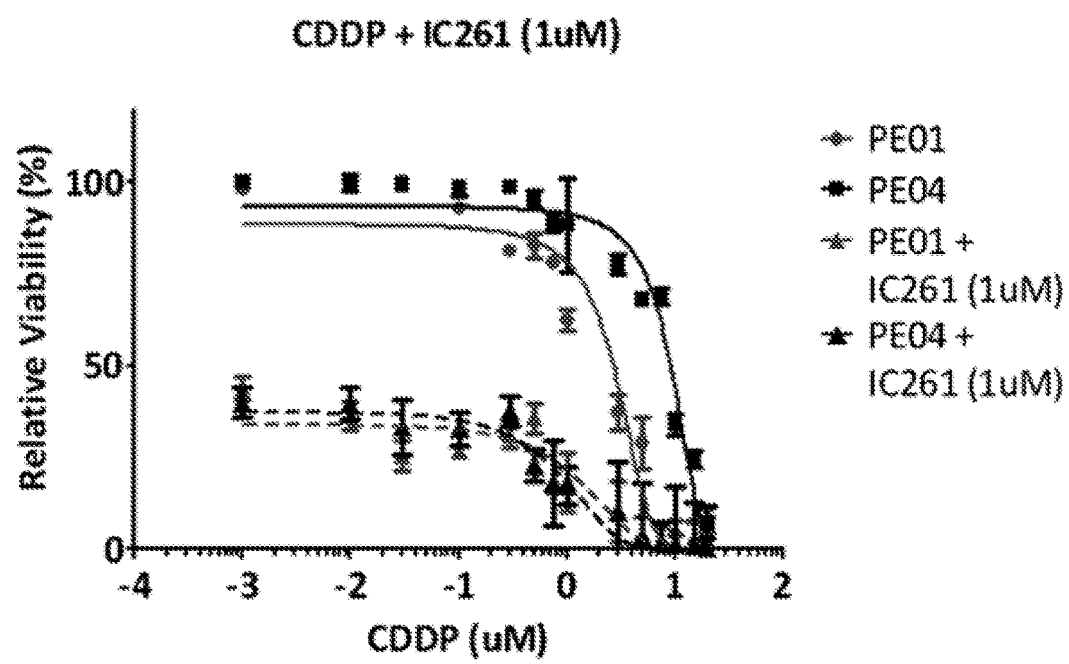
FIG. 13B graphically illustrates the relative cell viability of PE01 and PEO4 (cisplatin-resistant derivative) ovarian cancer cells in the presence of increasing doses of cisplatin (CDDP) when cultured in the presence of IC261; as described in Example 4.

Cisplatin, or cis-diamminedichloroplatinum(II) (CDDP), is a chemotherapy drug commonly used to treat numerous types of cancers including ovarian cancer. Cisplatin contains platinum complexes that crosslink DNA, ultimately triggering apoptosis of the cell. However, many treated cancer relapse and display a resistance to cisplatin. Considering the ability of CSNK1ε inhibitors to reduce viability of cells with amplified c-MYC expression, a similar role of CSNK1ε inhibitors on cisplatin resistant cancer cells was investigated. A2780 and A2780-CP70 (resistant derivative), PE01 and PE04 (resistant derivative of PE01) ovarian cancer cell lines were cultured in the presence of increasing doses of cisplatin and the presence or absence of IC261. Cell viability was monitored as described above. As illustrated in FIG. 13A, both A2780 and A2780-CP70 cells response to cisplatin was greatly sensitized by the addition of 1 μM IC-261. It is noted that the c-MYC expression level in A2780 cells is yet undetermined. As illustrated in FIG. 13B, PE01 and the resistant derivative PE04 ovarian cells, both with amplified c-MYC expression, also exhibited a large reduction in cell viability in the presence of low doses of cisplatin when also in the presence of 1 μM IC-261. These results indicate that inhibition of CSNK1ε with IC-261, or other CSNK1ε inhibitors, could be utilized in cases of chemotherapy resistant ovarian cancers.

Conclusion

This example demonstrates that CSNK1ε is required for the viability of ovarian cancer cells with amplified c-MYC expression. Consistent with the role observed in neuroblastoma cells, knockdown of CSNK1ε gene expression and function inhibition of CSNK1ε kinase activity results in reduced WNT signaling, indicating that WNT signaling mediates part of the CSNK1ε's effect on ovarian cell viability of cells with amplified c-MYC expression. Administration of the CSNK1ε inhibitor IC261 results in lower viability and proliferation in vitro and in vivo of ovarian cancer cells with amplified c-MYC expression. Therefore, these results demonstrate that CSNK1ε plays a vital role in the continued viability of MYC-driven ovarian cancers, and is a target for the treatment of MYC driven cancers and cancers otherwise resistant to cisplatin.

While the preferred embodiment of the invention has been illustrated and described, it will be appreciated that various changes can be made therein without departing from the spirit and scope of the invention.

The invention claimed is:

1. A method for inhibiting the growth and/or proliferation of a cisplatin resistant ovarian tumor cell having an amplified c-myc gene, comprising the step of contacting the cisplatin resistant ovarian tumor cell having the amplified c-myc gene with a casein kinase 1 epsilon (CSNK1ε) inhibitor.

2. The method of claim 1, wherein the tumor cell is contacted in vitro.

3. The method of claim 1, wherein the tumor cell is contacted in vivo in a mammalian subject.

4. The method of claim 1, wherein the CSNK1ε inhibitor is a small molecule inhibitor.

5. The method of claim 4, wherein the CSNK1ε inhibitor is selected from the group consisting of IC261, PF-4800567, and PF-670462.

6. A method of treating a subject suffering from a cisplatin resistant ovarian tumor comprising cisplatin resistant ovarian tumor cells having an amplified c-myc gene, comprising administering to the subject an amount of a composition comprising a casein kinase 1 epsilon (CSNK1ε) inhibitor effective to inhibit the growth and/or proliferation of the cisplatin resistant ovarian tumor cells having the amplified c-myc gene.

7. The method of claim 6, wherein the subject is further provided one or more additional anti-cancer therapies.

8. The method of claim 7, wherein the additional anti-cancer therapy comprises cisplatin.

9. The method of claim 6, wherein the CSNK1ε inhibitor is a small molecule inhibitor.

10. The method of claim 9, wherein the CSNK1ε inhibitor is selected from the group consisting of IC261, PF-4800567, and PF-670462.

11. The method of claim 6, further comprising the step of determining whether the tumor comprises tumor cells having an amplified c-myc gene prior to administering to said subject suffering from a tumor comprising tumor cells having the amplified c-myc gene said composition comprising a CSNK1ε inhibitor.

12. A method of treating cisplatin resistance in ovarian tumor cells comprising the steps of: (i) determining whether said tumor cells overexpress c-Myc and (ii) subsequently administering an effective amount of a casein kinase 1 epsilon (CSNK1ε) inhibitor to said cisplatin resistant ovarian tumor cells.

13. The method of claim 12, wherein the CSNK1ε inhibitor is a small molecule inhibitor.

14. The method of claim 13, wherein the small molecule inhibitor is IC261.

15. The method of claim 12, wherein the subject is further provided one or more additional anti-cancer therapies.

16. The method of claim 15, wherein the additional anti-cancer therapy comprises cisplatin.

17. A method of treating cisplatin resistance in ovarian tumor cells comprising the steps of: (i) determining whether said tumor cells have an amplified c-myc gene and (ii) subsequently administering an effective amount of a casein kinase 1 epsilon (CSNK1ε) inhibitor to said cisplatin resistant ovarian tumor cells.

18. The method of claim 17, wherein the CSNK1ε inhibitor is a small molecule inhibitor.

19. The method of claim 18, wherein the small molecule inhibitor is IC261.

20. The method of claim 17, wherein the subject is further provided one or more additional anti-cancer therapies.

21. The method of claim 20, wherein the additional anti-cancer therapy comprises cisplatin.

* * * * *